US009326996B2

(12) United States Patent
Franks et al.

(10) Patent No.: US 9,326,996 B2
(45) Date of Patent: May 3, 2016

(54) USE OF XENON AS NEUROPROTECTANT IN A NEONATAL SUBJECT

(71) Applicant: IMPERIAL INNOVATIONS LIMITED, London (GB)

(72) Inventors: Nicholas Peter Franks, London (GB); Mervyn Maze, London (GB)

( * ) Notice: Subject to any disclaimer, the term of this patent is extended or adjusted under 35 U.S.C. 154(b) by 0 days.

(21) Appl. No.: 14/618,667

(22) Filed: Feb. 10, 2015

(65) Prior Publication Data

US 2015/0216897 A1 Aug. 6, 2015

Related U.S. Application Data

(63) Continuation of application No. 11/667,065, filed as application No. PCT/GB2005/003253 on Aug. 19, 2005, now abandoned.

(30) Foreign Application Priority Data

Aug. 19, 2004 (GB) .................................. 0418540.1

(51) Int. Cl.
*A61K 31/08* (2006.01)
*A61K 33/00* (2006.01)
*A61K 45/06* (2006.01)

(52) U.S. Cl.
CPC ................ *A61K 33/00* (2013.01); *A61K 31/08* (2013.01); *A61K 45/06* (2013.01)

(58) Field of Classification Search
CPC ... A61K 2300/00; A61K 31/08; A61K 33/00; A61K 45/06
See application file for complete search history.

(56) References Cited

U.S. PATENT DOCUMENTS 6,653,354 B2 * 11/2003 Franks et al. ................ 514/769
7,390,508 B2    6/2008 Franks et al.
7,632,872 B2   12/2009 Franks et al.

FOREIGN PATENT DOCUMENTS

DE      199 33 704 A1    1/2001
WO      WO 02/22116 A1   3/2002
WO         03/092707 A1  11/2003
WO      WO 2004/012749   2/2004

OTHER PUBLICATIONS

Lane et al. (Science, 1980; 210(21):899-901).*
Ikonomidou et al. (Science 1999, 283:70-74).*
Todorovic et al. (The Journal of Neuroscience. 2003;23(3):876-882).*
Pinnock (Fundamentals of Anaesthesia 2003, Cambridge University Press; pp. 592-593).*
Carvallo et al. (European Cells and Materials 2004; 7(suppl2):58-59).*
International Search Report (ISR) from PCT/GB2005/003253.
(Continued)

*Primary Examiner* — Ernst V Arnold
(74) *Attorney, Agent, or Firm* — Hodgson Russ LLP

(57) ABSTRACT

The present invention relates to the use of xenon in the preparation of a medicament for preventing and/or alleviating one or more anesthetic-induced neurological deficits in a neonatal subject.
The present invention further relates to combinations of xenon and sevoflurane, and use thereof as preconditioning agents for administration prior to hypoxic-ischaemic injury.

8 Claims, 13 Drawing Sheets

(56) References Cited

OTHER PUBLICATIONS

Nagata et al., "Xenin inhibits but N2O enhances ketamine-induced c-Fos expression in the rat posterior cingulate and retrospinal cortices," *Anesthesia and Analgesia*, vol. 92, No. 2, Feb. 2001, pp. 362-368.

Hecker et al., "Minimum anesthetic concentration of sevoflurane with different xenon concentrations in swine," *Anesthesia and Analgesia*, vol. 97, No. 5, Nov. 2003, pp. 1367-1369.

Goto et al., Thermoregulatory thresholds for vasoconstriction in patients anesthetized with various 1-minimum alveolar concentration combinations of xenon, nitrous oxide, and isoflurane, *Anesthesia and Analgesia*, Philadelphia, PA, vol. 91, No. 3, Sep. 1999, pp. 626-632.

Wise-Faberowski et al., "Desflurane and sevoflurane attenuate oxygen and glucose deprivation-induced neuronal cell death," Database Medline Online, U.S. National Library of Medicine, Jul. 2003, Database, accession No. NLM12826966 abstract (one page).

Wilhelm et al., "Effects of Xenon on In Vitro and In Vivo Models of Neuronal Injury," *Anesthesiology, Americal Society of Anesthiologists*, Philadelphia, PA, vol. 96, No. 6, Jun. 2002, pp. 1485-1488.

Ma et al., "Neuroprotective and neurotoxic properties of the 'inert' gas, xenon," *British Journal of Neuroscience: The Official Journal of the Society for Neuroscience*, Feb. 2003, vol. 89, No. 5, pp. 739-746.

Jevtovic-Todorovic et al., "Early exposure to common anesthetic agents causes widespread neurodegeneration in the developing rat brain and persistent learning deficits," The Journal of Neuroscience: The Official Journal of the Society for Neuroscience, Feb. 2003, vol. 23, No. 3, pp. 876-882.

Fukura et al., "Nitrous Oxide, But Not Xenon, Affects the Signaling in the Neuronal Growth Cone", Prog. Neuro-Psychopharmacol. & Biol. Psychiat. 2000, vol. 24, pp. 1357-1368.

Kelsall et al., "Reversible Neurologic Dysfunction Following Isoflurane Seda in Pediatric Intensive Care", Abstract of Crit Care Med 1994, 22(6), 1 page.

Picker et al., "Xenon Increases Total Body Oxygen Consumption During Isoflurane Anaesthesia in Dogs", British Journal of Anaesthesia 2002, 88(4), pp. 546-554.

\* cited by examiner

USE OF XENON AS NEUROPROTECTANT IN A NEONATAL SUBJECT

The present invention relates to the field of anesthetics. More specifically, the invention relates to anesthetic agents suitable for use in newborn and/or fetal subjects.

BACKGROUND TO THE INVENTION

Xenon's anesthetic properties have been known to the medical profession for over 50 years (Cullen and Gross, 1951). However, despite some impressive displays of clinical efficacy in patients (Luttropp et al., 1994; Lynch et al., 2000), everyday use of xenon anesthesia has failed to materialize. This is largely associated with the significant cost involved in production of xenon through fractional distillation of liquid air, and hence the relatively small percentage of the total refined quantity of xenon available for anesthesia (Hanne Marx et al., 2001). Consequently, use of xenon is likely to be restricted to special areas where there is an appreciable cost-benefit advantage. One such area may be neonatal anesthesia, where xenon may lack harmful side effects seen with other commonly used neonatal anesthetics e.g. nitrous oxide (Layzer, 1978; Amos et al., 1982; Jevtovic-Todorovic et al., 1998).

It is well documented in the art that neonatal insults cause long lasting effects (Anand and Scalzo, 2000; Balduini et al., 2000; Jevtovic-Todorovic et al., 2003). Therefore it is sensible to adopt a degree of caution when using drugs in the neonate which could potentially alter neurodevelopment (such as alcohol, phencyclidine, ketamine, $N_2O$, isoflurane, benzodiazepines, barbiturates and anticonvulsants (Olney et al., 2002d) by causing apoptotic neurodegeneration). This is especially true given that often only a single exposure is required, even at anesthetic doses (Ikonomidou et al., 2001; Young et al., 2003).

Normal Neurodevelopment

Normal neurodevelopment is a carefully regulated (Butler, 1999) sequence of events including proliferation, differentiation, migration and synaptogenesis. Glutamate is thought to have a role in all of these processes (Ikonomidou and Lechoslaw, 2002), for example high concentrations of glutamate at migration target zones suggests a role as a neuronal chemoattractant (Behar et al., 1999) along with the NMDA receptor used to detect it (Komuro and Rakie, 1993). The intriguing finding of specific NMDA receptor subtypes (e.g. NR2B and NR2D) in different anatomical regions may shed light on the precise nature of migration control (Behar et al., 1999). From work by the same group, it is also apparent that different species employ different mediators in migration control—currently either GABA (rats) or glutamate (mice) (Behar et al., 2001).

Synaptogenesis (the brain growth spurt) is a period of a rapid establishment of synapses, characterised by a high level of physiological cell death (up to 1% (Olney et al., 2002b)). This includes the formation of extensive corticothalamic and thalamocortical projections (Molar and Blakemore, 1995). Despite the immense complexity of inter-species embryology, it has been shown that comparisons can be made because milestones in neurodevelopment tend to occur in the same sequence (Clancy et al., 2001). This permits an extrapolation of the period of peak synaptogenic activity from the 7 day old rat pup (Olney et al., 2002a) to a 0-8 month old human being (Ikonomidou et al., 1999; Jevtovic-Todorovic et al., 2003). However, based on analysis of NMDA receptor subtypes, it is more probable that humans experience an extended period of synaptogenesis—from the beginning of the $3^{rd}$ trimester of pregnancy to several years old (Dobbing and Sands, 1979; Jevtovic-Todorovic et al., 2003).

Apoptosis in the Developing Nervous System

Apoptosis, first formally described in 1972 (Kerr et al., 1972), is an essential feature of normal neurodevelopment in processes such as sculpturing, trimming, control of cell numbers and cellular disposal. It is characterised as "active cell death" comprising initiation, commitment and execution by dedicated cellular proteins (Sloviter, 2002). The crucial role of apoptosis is highlighted by the fact that genetic upregulation or downregulation of apoptosis results in a lethal genotype (Yoshida et al., 1998; Rinkenberger et al., 2000).

Control of physiological cell death (PCD) in the immature CNS is currently thought to be governed by the neurotrophic hypothesis—whereby neurones which fail to reach their survival promoting synaptic targets (Sherrard and Bower, 1998) initiate a specialised form of cell suicide secondary to withdrawal of environmental trophic support (Young et al., 1999) (via both neurotrophins and electrical stimulation) (Brenneman et al., 1990). Due to the complex divergent and convergent nature of the "survival pathway" many ligands and mechanisms are involved in maintaining neuronal survival. The cytosol and mitochondria of neurones field a balanced assortment of molecules which are either anti-apoptotic (e.g. Bcl-2 and cAMP response binding protein) or pro-apoptotic (e.g. Bad, Bax and the caspase family) which determine cell fate. Bcl-2 and its associated peptides are thought to be particularly important in the developing CNS (Yuan and Yanker, 2000), as evidenced by the high levels of expression in the neonate and the fact that experimental over-expression of Bcl-2 can both override lack of trophic support (Garcia et al., 1992), and even prevent PCD altogether (Martinou et al., 1994). A variant of Bcl-2 (Bcl-$X_L$) may have a specialised role in maintaining developing neurones before they have found their synaptic targets (Motoyama et al., 1995).

Neurodegeneration in Neonates

In 1999, data were published showing that use of NMDA receptor antagonists in neonatal rats produced specific patterns of neurodegeneration (distinct from glial cells) (Ikonomidou et al., 1999). On electron microscopy, this neurodegeneration was identical to apoptotic cell death, and most evident in the laterodorsal thalamic nucleus, one of the areas of the brain implicated in learning and memory (Goen et al., 2002). This phenomenon has since been demonstrated in other brain regions with other drugs (Monti and Contestabile, 2000).

Later work done by Jevtovic-Todorovic et al. showed that neonatal rats are vulnerable to harmful side effects of anesthesia during the synaptogenic period. They demonstrated up to a 68-fold increase in the number of degenerating neurones above baseline in areas such as the laterodorsal and anteroventral thalamic nuclei (and to some extent layer II of the parietal cortex) after exposure to anesthetic agents (Jevtovic-Todorovic et al., 2003), which resulted in a functional neurological deficit in behaviour tests later in life. Specifically, the GABAergic anesthetic isoflurane (Gyulai et al., 2001), produced dose-dependent neurodegeneration in its own right, with synergistic neurodegeneration with the successive addition of midazolam (a double GABAergic cocktail) and then $N_2O$ (a triple cocktail) (Jevtovic-Todorovic et al., 2003). This process has been shown to occur with exposure to GABAergic agents in areas other than anesthesia, such as anticonvulsant therapy and maternal drug abuse in rats (Bittigau et al., 2002; Farber and Olney, 2003).

A clinical manifestation of this type of neurodegeneration is detected in 1 to 2 infants per 1000 livebirths as Fetal Alcohol Syndrome (FAS) (Moore and Persaud, 1998)—characterised by abnormal facial features, microencephaly and mental retardation (Olney et al., 2002c). It is thought that binge drinking by pregnant mothers produces very high levels of ethanol (a dual GABAergic agent and NMDA receptor antagonist (Farber and Olney, 2003)) in the fetal brain, which in turn triggers the type of neurodegeneration discussed above (Ikonomidou et al., 2000). It is worth noting that this mechanism of action closely resembles that of current anesthetic procedures.

The present invention seeks to provide an anesthetic agent suitable for use in the newborn that is safe, efficacious, and does not have any adverse effects on neurodevelopment. More specifically, the invention seeks to provide an anesthetic agent for neonatal subjects that is suitable for use in combination with other anesthetics know to adversely affect neurodevelopment. In particular, the invention seeks to provide anesthetic combinations for use in neonates which comprise an agent capable of preventing or alleviating the adverse effects of known anesthetic agents such as isoflurane and/or sevoflurane, and/or desflurane.

STATEMENT OF INVENTION

In a broad aspect, the present invention relates to the use of xenon for treating and/or preventing and/or alleviating one or more anesthetic-induced neurological deficits in a subject, preferably a neonatal subject.

Various aspects of the invention are set forth in accompanying claims and in the detailed description below.

DETAILED DESCRIPTION

A first aspect of the invention relates to the use of xenon in the preparation of a medicament for treating and/or preventing and/or alleviating one or more anesthetic-induced neurological deficits in a subject, preferably a neonatal subject.

It is well documented in the art that exposure to anesthetics, including NMDA receptor antagonists such as $N_2O$, ketamine and other agents such as isoflurane, triggers apoptotic neurodegeneration during the synaptogenic phase of brain development.

Studies have demonstrated that xenon, itself an NMDA receptor antagonist, not only lacks the characteristic toxicity produced by ketamine and $N_2O$ in adult rats, but also ameliorates their toxicity. The experiments detailed herein have investigated xenon's properties in a neonatal rat model of neurodegeneration.

An in vivo rat model of anesthesia was used in conjunction with both histology and immunohistochemistry to identify and quantify apoptosis induced by various combinations of anesthetic agents. Unlike isoflurane, xenon did not induce any apoptotic neurodegeneration above the baseline observed in controls. Additionally, it was found that whilst nitrous oxide enhances isoflurane-induced apoptosis, xenon reduces the degree of injury.

By way of summary, seven day old Sprague-Dawley rats were exposed to 25% oxygen along with one of several gas combinations (75% nitrogen, 75% nitrous oxide, 75% xenon, 0.75% isoflurane, 75% nitrous oxide+0.75% isoflurane, 60% xenon+0.75% isoflurane) for 6 hours (n=3-5/group). The rats were sacrificed after anesthesia, and their brains processed to assess the severity of apoptosis (using caspase-3 immunohistochemistry, c-Fos immunohistochemistry, and DeOlmos silver staining).

When administered alone, neither $N_2O$ nor xenon caused a significant increase in caspase-3 positive cells in the hippocampus or cortex (cortical values: 22.5±5.9 and 19.7±9.6 respectively vs 19.3±6.4 in controls; p>0.05). In contrast, isoflurane alone significantly increased the number of degenerating neurones in both regions (76.5±11.4; p<0.01). Similarly, sevoflurane alone caused a significant increase in degenerating neurons from a control value of 20.0±2 positive cells to 42±2 positive cells when 1.5% sevoflurane was administered. When combined with isoflurane, $N_2O$ considerably enhanced isoflurane-induced apoptosis (232.0±19.9; p<0.001 vs air) while xenon reduced the injury (26.7±3.9; p>0.05 vs air).

These data suggest that xenon, unlike other anesthetics that exhibit NMDA receptor blockade, does not enhance apoptotic neurodegeneration in the neonatal rat. In fact, xenon appears to protect against isoflurane-induced apoptosis.

As used herein, the term "neonatal subject" refers to a newborn subject. Preferably the neonatal subject is a mammal in the first four weeks after birth. More preferably, the neonatal subject is a mammal in the first two weeks, more preferably still, the first week after birth.

Even more preferably, the neonatal subject is a human.

In one preferred embodiment, the neonatal subject is a subject which is undergoing, or requires, fetal surgery.

In one preferred embodiment, the neonatal subject is a subject having a life-threatening condition requiring emergent or elective surgery later in life In another preferred embodiment, the neonatal subject receives xenon indirectly as part of an anesthetic or analgesic regimen administered to the mother during labour, or during cesarean section.

Preferably, the medicament is for preventing and/or alleviating one or more anesthetic-induced neurological deficits in a subject, preferably a neonatal subject.

As used herein, the term "preventing and/or alleviating neurological deficits" refers to reducing the severity of one or more neurological deficits as compared to a subject having undergone treatment with an anesthetic in the absence of xenon.

Preferably, the neurological deficit is a learning, memory, neuromotor, neurocognitive and/or psychocognitive deficit.

In an even more preferred embodiment, the neurological deficit may be a neuromotor or neurocognitive, deficit. As used herein the term "neuromotor deficit" is given its meaning as understood by the skilled artisan so as to include deficits in strength, balance and mobility. Similarly, the term "neurocognitive deficit" is given its meaning as understood by the skilled artisan so as to include deficits in learning and memory. Such neurocognitive deficits may typically be assessed by well-established criteria such as the short-story module of the Randt Memory Test [Randt C, Brown E. Administration manual: Randt Memory Test. New York: Life Sciences, 1983], the Digit Span subtest and Digit Symbol subtest of the Wechsler Adult Intelligence Scale-Revised [Wechsler D. The Wechsler Adult Intelligence Scale-Revised (WAIS-R). San Antonio, Tex.: Psychological Corporation, 1981.], the Benton Revised Visual Retention Test [Benton A L, Hansher K. Multilingual aphasia examination. Iowa City: University of Iowa Press, 1978] and the Trail Making Test (Part B) [Reitan R M. Validity of the Trail Making Test as an indicator of organic brain damage. Percept Mot Skills 1958; 8:271-6]. Other suitable neuromotor and neurocognitive tests are described in Combs D, D'Alecy L: Motor performance in rats exposed to severe forebrain ischemia: Effect of fasting and 1,3-butanediol. Stroke 1987; 18: 503-511 and Gionet T, Thomas J, Warner D, Goodlett C, Wasserman E, West J: Forebrain ischemia induces selective behavioral impairments associated with hippocampal injury in rats. Stroke 1991; 22: 1040-1047).

In one preferred embodiment, the neurological deficit is neurodegeneration.

As used herein, the term "neurodegeneration" refers to cell shrinkage, chromatin-clumping with margination and formation of membrane-enclosed apoptotic bodies; on application of caspase 3 antibody the neurodegenerating neurones stain black on application of 3,3'-diamino-benzidine (dab).

In another preferred embodiment, the neurological deficit is associated with neuronal apoptosis.

In another preferred embodiment, the neurological deficit is associated with neuronal necrosis.

In another preferred embodiment, the neurological deficit is a learning, memory, neuromotor or psychocognitive deficit.

A second aspect of the invention relates to the use of xenon in the preparation of a medicament for treating and/or alleviating and/or preventing anesthetic-induced neurodegeneration in a subject, preferably a neonatal subject.

A third aspect of the invention relates to the use of xenon in the preparation of a medicament for treating and/or alleviating and/or preventing anesthetic-induced neuronal apoptosis in a subject, preferably a neonatal subject.

A third aspect of the invention relates to the use of xenon in the preparation of a medicament for preventing and/or alleviating anesthetic-induced neuronal injury in a subject, preferably a neonatal subject.

For all of the above aspects, preferably the anesthetic is a volatile anesthetic agent. Examples of volatile anesthetics include isoflurane, sevoflurane and desflurane.

For all of the above aspects, preferably the anesthetic is either a GABAergic agent such as isoflurane, sevoflurane or desflurane, or an NMDA receptor antagonist anesthetic (eg ketamine or nitrous oxide).

More preferably, the anesthetic is isoflurane, sevoflurane, or desflurane.

Isoflurane is a halogenated volatile anesthetic which induces and maintains general anesthesia by depression of the central nervous system and resultant loss of consciousness. Throughout maintenance of anesthesia, a high proportion of the isoflurane is eliminated by the lungs. When administration is stopped, the bulk of the remaining isoflurane is eliminated unchanged from the lungs. As solubility of isoflurane is low, recovery from isoflurane anesthesia in man is rapid.

As isoflurane has a mild pungency, inhalation is usually preceded by the choice of a short-acting barbiturate, or other intravenous induction agent, to prevent coughing. Isoflurane can induce increased salivation and coughing in small children upon administration. Adverse reactions encountered with isoflurane are similar to those observed with other halogenated anesthetics and include hypotension, respiratory depression and arrhythmias. Other minor side-effects encountered while using isoflurane are an increase in the white blood cell count (even in the absence of surgical stress) and also shivering, nausea and vomiting during the post-operative period. There have also been rare reports of mild, moderate and severe (some fatal) post-operative hepatic dysfunction. The causal relationship for this is unknown.

Isoflurane causes an increase in cerebral blood flow at deeper levels of anesthesia; this may give rise to an increase in cerebral spinal fluid pressure. Where appropriate, this can be prevented or reversed by hyperventilating the patient before or during anesthesia. As with other halogenated anesthetics, isoflurane must be used with caution in patients with increased intracranial pressure.

Isoflurane is a powerful systemic and coronary arterial dilator. The effect on systemic arterial pressure is easily controlled in the normal healthy patient and has been used specifically as a means of inducing hypotension. However, the phenomenon of "coronary steal" means that isoflurane should be used with caution in patients with coronary artery disease. In particular, patients with subendocardial ischaemia might be anticipated to be more susceptible.

Sevoflurane, a fluorinated methyl-isopropyl ether is relatively pleasant and non-pungent and is used to cause general anesthesia before and during surgery. It is administered by inhalation. As it has a blood/gas partition coefficient of only 0.6, onset and recovery times are fast.

The dose of sevoflurane required varies from patient to patient, depending on age, physical condition, interactions with other medicines and the type of surgery being performed. Side effects include bradycardia, hypotension, tachycardia, agitation, laryngospasm, airway obstruction, cough, dizziness, drowsiness, increased amount of saliva, nausea, shivering, vomiting, fever, hypothermia, movement, headache. As sevoflurane is metabolized very slowly in the human body there is a high risk of renal toxicity. When used in children sevoflurane has been known to cause increased agitation.

In the context of the present invention, xenon may be administered to the subject simultaneously, in combination, sequentially or separately with the anesthetic agent.

As used herein, "simultaneously" is used to mean that the xenon is administered concurrently with the anesthetic agent, whereas the term "in combination" is used to mean the xenon is administered, if not simultaneously, then "sequentially" within a timeframe in which the xenon and the anesthetic both exhibit a therapeutic effect, i.e. they are both are available to act therapeutically within the same time-frame. Thus, administration "sequentially" may permit the xenon to be administered within 5 minutes, 10 minutes or a matter of hours before or after the anesthetic.

In one particularly preferred embodiment, the xenon is administered to the subject prior to the volatile anesthetic agent. Studies have indicated that xenon is capable of changing the vulnerability of the subject to all kinds of injury of an apoptotic or necrotic variety.

In one preferred embodiment the xenon is administered before hypoxic-ischaemic injury or any other injury which is apoptosis-dependent (i.e. in which apoptosis is the pathway to cell death) or necrosis-dependent (i.e. in which necrosis is the pathway to cell death), i.e. the xenon functions as a preconditioning agent.

In another particularly preferred embodiment, the xenon is administered after the volatile anesthetic agent. Thus, in one preferred embodiment the xenon is administered after hypoxic-ischaemic injury or any other injury which is apoptosis-dependent (i.e. in which apoptosis is the pathway to cell death) or necrosis-dependent (i.e. in which necrosis is the pathway to cell death).

In contrast to "in combination" or "sequentially", "separately" is used herein to mean that the gap between administering the xenon and exposing the subject to anesthetic agent is significant i.e. the xenon may no longer be present in the bloodstream in a therapeutically effective amount when the subject is exposed to the anesthetic agent, or the anesthetic may no longer be present in the bloodstream in a therapeutically effective amount when the subject is exposed to the xenon.

More preferably, the xenon is administered sequentially or simultaneously with the anesthetic agent, more preferably simultaneously.

More preferably, the xenon is administered prior to, or simultaneously with, the anesthetic agent, more preferably simultaneously.

In one preferred embodiment of the invention, the xenon is administered in a therapeutically effective amount.

In another preferred embodiment, the xenon is administered in a sub-therapeutically effective amount. In this context, the term "sub-therapeutically effective amount" means an amount which is lower than that typically required to produce anesthesia. Generally, an atmosphere of about 70% xenon is sufficient to induce or maintain anesthesia. Accordingly, a sub-therapeutic amount of xenon corresponds to less than about 70% xenon.

Even more preferably, the combination of xenon and anesthetic agent has a synergistic effect, i.e., the combination is synergistic.

Another aspect of the invention relates to the use of (i) xenon, and (ii) an anesthetic selected from isoflurane, sevoflurane and desflurane, in the preparation of a medicament for alleviating and/or preventing isoflurane-induced and/or sevoflurane-induced and/or desflurane-induced neuronal injury in a subject, preferably a neonatal subject.

Another aspect of the invention relates to the use of (i) xenon, and (ii) isoflurane, in the preparation of a medicament for alleviating and/or preventing isoflurane-induced neuronal injury in a subject, preferably a neonatal subject.

Another aspect of the invention relates to the use of (i) xenon, and (ii) sevoflurane, in the preparation of a medicament for alleviating and/or preventing sevoflurane-induced neuronal injury in a subject, preferably a neonatal subject.

Another aspect of the invention relates to the use of (i) xenon, and (ii) desflurane, in the preparation of a medicament for alleviating and/or preventing desflurane-induced neuronal injury in a subject, preferably a neonatal subject.

Yet another aspect of the invention relates to the use of xenon in the preparation of a medicament for alleviating and/or preventing isoflurane-induced and/or sevoflurane-induced and/or desflurane-induced neuronal injury in a subject, preferably a neonatal subject.

Yet another aspect of the invention relates to the use of (i) xenon, and (ii) an anesthetic selected from isoflurane, sevoflurane and desflurane, in the preparation of a medicament for providing anesthesia in a subject, preferably a neonatal subject, wherein the amount of xenon is sufficient to alleviate or prevent anesthetic-induced injury.

Another aspect of the invention relates to the use of xenon and isoflurane in the preparation of a medicament for providing anesthesia in a subject, preferably a neonatal subject, wherein the amount of xenon is sufficient to alleviate or prevent isoflurane-induced neuronal injury.

Another aspect of the invention relates to the use of xenon and sevoflurane in the preparation of a medicament for providing anesthesia in a subject, preferably a neonatal subject, wherein the amount of xenon is sufficient to alleviate or prevent sevoflurane-induced neuronal injury.

Another aspect of the invention relates to the use of xenon and desflurane in the preparation of a medicament for providing anesthesia in a subject, preferably a neonatal subject, wherein the amount of xenon is sufficient to alleviate or prevent desflurane-induced neuronal injury.

For all of the above aspects, preferably the xenon is administered in combination with a pharmaceutically acceptable diluent, excipient and/or carrier.

Examples of such suitable excipients for the various different forms of pharmaceutical compositions described herein may be found in the "Handbook of Pharmaceutical Excipients", $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers and dyes may be provided in the pharmaceutical composition. Examples of preservatives include sodium benzoate, sorbic acid and esters of p-hydroxybenzoic acid. Antioxidants and suspending agents may be also used.

The xenon may also be administered in combination with another pharmaceutically active agent. The agent may be any suitable pharmaceutically active agent including anesthetic or sedative agents which promote GABAergic activity. Examples of such GABAergic agents include propofol and benzodiazapines.

The xenon may also be administered in combination with other active ingredients such as L-type calcium channel blockers, N-type calcium channel blockers, substance P antagonists, sodium channel blockers, purinergic receptor blockers, or combinations thereof.

The xenon may be administered by any suitable delivery mechanism, or two or more suitable delivery mechanisms.

In one particularly preferred embodiment, the xenon is administered by perfusion. In the context of the present invention, the term "perfusion" refers to the introduction of an oxygen/xenon mixture into, and the removal of carbon dioxide from, a patient using a specialised heart-lung machine. In general terms, the heart-lung machine replaces the function of the heart and lungs and provides a bloodless, motionless surgical field for the surgeon. The perfusionist ventilates the patient's blood to control the level of oxygen and carbon dioxide. In the context of the present invention, the perfusionist also introduces xenon into the patient's blood. The perfusionist then propels the blood back into the arterial system to provide nutrient blood flow to all the patient's vital organs and tissues during heart surgery.

In one preferred embodiment, the medicament is in gaseous form.

In another highly preferred embodiment, the xenon is administered by inhalation.

In one preferred embodiment, the medicament further comprises oxygen, nitrogen or mixtures thereof, more particularly air.

In another preferred embodiment, the medicament further comprises helium, NO, CO, $CO_2$, $N_2O$, other gaseous compounds and/or inhalable medicaments.

In another preferred embodiment, the xenon is mixed with another inert gas, such as argon or krypton.

In another preferred embodiment, the xenon is mixed with oxygen, or an oxygen-containing gas.

In one highly preferred embodiment, the medicament is a binary gaseous mixture which comprises from about 10 to about 80% xenon by volume, more preferably from about 20 to about 80% xenon by volume, with the remainder comprising oxygen. In another preferred embodiment, the medicament comprises from about 30 to about 75% xenon by volume, with the remainder comprising oxygen.

In another highly preferred embodiment, the medicament is a ternary gaseous mixture which comprises from about 10 to about 80% xenon by volume, more preferably from about 20 to about 80% xenon by volume, with the remainder comprising oxygen and nitrogen. In another preferred embodiment, the medicament comprises from about 30 to about 75% xenon by volume, with the remainder comprising oxygen and nitrogen.

In another preferred embodiment, the medicament comprises about 5 to about 90% by volume of xenon, more preferably, about 10 to about 80% by volume of xenon, more preferably still, about 10 to about 50% by volume of xenon, more preferably still, about 10 to about 30% by volume of xenon.

In another preferred embodiment, the medicament is in the form of a liquid or solution. In one particularly preferred embodiment, the medicament is in the form of a lipid emulsion.

Preferably, the liquid is administered in the form of a solution or an emulsion prepared from sterile or sterilisable solutions, which may be injected intravenously, intraarterially, intrathecally, subcutaneously, intradermally, intraperitoneally or intramuscularly.

In one particularly preferred embodiment, the xenon is administered in the form of a lipid emulsion. The intravenous formulation typically contains a lipid emulsion (such as the commercially available Intralipid®10, Intralipid®20, Intrafat®, Lipofundin®S or Liposyn® emulsions, or one specially formulated to maximise solubility) which sufficiently increases the solubility of the xenon to achieve the desired clinical effect. Further information on lipid emulsions of this sort may be found in G. Kleinberger and H. Pamperl, Infusionstherapie, 108-117 (1983) 3.

The lipid phase of the present invention which dissolves or disperses the gas is typically formed from saturated and unsaturated long and medium chain fatty acid esters containing 8 to 30 carbon atoms. These lipids form liposomes in aqueous solution. Examples include fish oil, and plant oils such as soya bean oil, thistle oil or cottonseed oil. The lipid emulsions of the invention are typically oil-in-water emulsions wherein the proportion of fat in the emulsion is conventionally 5 to 30% by weight, and preferably 10 to 20% by weight. Oil-in-water emulsions of this sort are often prepared in the presence of an emulsifying agent such as a soya phosphatide.

The lipids which form the liposomes of the present invention may be natural or synthetic and include cholesterol, glycolipids, sphingomyelin, glucolipids, glycosphingolipids, phosphatidylcholine, phosphatidylethanolamine, phosphatidyl-serine, phosphatidylglycerol, phosphatidylinositol.

The lipid emulsions of the present invention may also comprise additional components. These may include antioxidants, additives which make the osmolarity of the aqueous phase surrounding the lipid phase isotonic with the blood, or polymers which modify the surface of the liposomes.

It has been established that appreciable amounts of xenon maybe added to a lipid emulsion. Even by the simplest means, at 20° C. and normal pressure, xenon can be dissolved or dispersed in concentrations of 0.2 to 10 ml or more per ml of emulsion. The concentration of dissolved gas is dependent on a number of factors, including temperature, pressure and the concentration of lipid.

The lipid emulsions of the present invention may be loaded with gaseous xenon. In general, a device is filled with the emulsion and anesthetics as gases or vapours passed through sintered glass bubblers immersed in the emulsion. The emulsion is allowed to equilibrate with the anesthetic gas or vapour at a chosen partial pressure. When stored in gas tight containers, these lipid emulsions show sufficient stability for the anesthetic not to be released as a gas over conventional storage periods.

The lipid emulsions of the present invention may be loaded so that the xenon is at the saturation level. Alternatively, the xenon may be present in lower concentrations, provided, for example, that the administration of the emulsion produces the desired pharmaceutical activity.

The concentration of xenon employed in the invention may be the minimum concentration required to achieve the desired clinical effect. It is usual for a physician to determine the actual dosage that will be most suitable for an individual patient, and this dose will vary with the age, weight and response of the particular patient. There can, of course, be individual instances where higher or lower dosage ranges are merited, and such are within the scope of this invention.

Preferably, the medicament is in a form suitable for intravenous, neuraxial or transdermal delivery.

A further aspect of the invention relates to a method of preventing and/or alleviating anesthetic-induced neurological deficits in a subject, preferably a neonatal subject, said method comprising administering a therapeutically effective amount of xenon to said subject.

A further aspect of the invention relates to a method of treating and/or alleviating and/or preventing anesthetic-induced neurodegeneration in a subject, preferably a neonatal subject, said method comprising administering a therapeutically effective amount of xenon to said subject.

A further aspect of the invention relates to a method of treating and/or alleviating and/or preventing anesthetic-induced neuronal apoptosis in a subject, preferably a neonatal subject, said method comprising administering a therapeutically effective amount of xenon to said subject.

A further aspect of the invention relates to a method of treating and/or alleviating and/or preventing anesthetic-induced neuronal injury in a subject, preferably a neonatal subject, said method comprising administering a therapeutically effective amount of xenon to said subject.

A method of preventing and/or alleviating isoflurane-induced neuronal injury in a subject, preferably a neonatal subject, said method comprising administering to said subject xenon and isoflurane.

A method of preventing and/or alleviating sevoflurane-induced neuronal injury in a subject, preferably a neonatal subject, said method comprising administering to said subject xenon and sevoflurane.

A method of preventing and/or alleviating desflurane-induced neuronal injury in a subject, preferably a neonatal subject, said method comprising administering to said subject xenon and desflurane.

A method of providing anesthesia and/or analgesia in a subject, preferably a neonatal subject, said method comprising administering xenon in combination with isoflurane, wherein the amount of xenon is sufficient to alleviate and/or prevent isoflurane-induced neuronal injury.

A method of providing anesthesia and/or analgesia in a subject, preferably a neonatal subject, said method comprising administering xenon in combination with sevoflurane, wherein the amount of xenon is sufficient to alleviate and/or prevent sevoflurane-induced neuronal injury.

A method of providing anesthesia and/or analgesia in a subject, preferably a neonatal subject, said method comprising administering xenon in combination with desflurane, wherein the amount of xenon is sufficient to alleviate and/or prevent desflurane-induced neuronal injury.

Preferred embodiments for all of the above methods are identical to those given above for the corresponding use aspects.

Yet another aspect of the invention relates to an anesthetic formulation for preventing and/or alleviating one or more anesthetic-induced neurological deficits in a subject, preferably a neonatal subject, said formulation comprising xenon and a pharmaceutically acceptable diluent, excipient and/or carrier.

Yet another aspect of the invention relates to an anesthetic formulation for treating and/or alleviating and/or preventing anesthetic-induced neurodegeneration in a subject, preferably a neonatal subject, said formulation comprising xenon and a pharmaceutically acceptable diluent, excipient and/or carrier.

A further aspect of the invention relates to an anesthetic formulation for treating and/or alleviating and/or preventing anesthetic-induced neuronal apoptosis in a subject, preferably a neonatal subject, said formulation comprising xenon and a pharmaceutically acceptable diluent, excipient and/or carrier.

A further aspect of the invention relates to an anesthetic formulation for treating and/or alleviating and/or preventing anesthetic-induced neuronal necrosis in a subject, preferably a neonatal subject, said formulation comprising xenon and a pharmaceutically acceptable diluent, excipient and/or carrier.

In a preferred embodiment, the anesthetic formulation of the invention further comprises an anesthetic agent.

More preferably, the anesthetic agent is a GABAergic agent.

Even more preferably, the anesthetic agent is isoflurane, sevoflurane or desflurane.

Another aspect of the invention relates to an anesthetic formulation comprising 60% xenon, 0.75% isoflurane, 25% oxygen and with the balance as nitrogen.

Xenon

As an anesthetic gas, xenon exhibits many desirable qualities including cardiostability (Stowe et al., 2000), a low blood-gas coefficient (Nakata et al., 1997) (the explanation for xenon's fast induction and emergence times), and a potent analgesic effect (Ma et al., 2004). Given the inevitable restricted application of this extremely rare and costly gas, xenon may find a niche as a prophylactic intra-operative neuroprotective anesthetic (Mayumi Homi et al., 2003).

The neuroprotective effects of xenon have been observed in in vivo models of acute neuronal injury involving administration of excitotoxins to rats (Ma et al 2002), cardiopulmonary bypass in rats (Ma et al 2003b), middle cerebral artery occlusion in mice (Homi et al, 2003), cardiac arrest in pigs (Schmidt et al 2005), and hypoxia-ischaemia in neonatal rats (Ma et al, 2005). Xenon was a more efficacious neuroprotective agent than either gavestinel (Ma et al, 2005) or dizolcipine (Ma et al 2003a), two other NMDA antagonists that have been clinically tested.

In vitro work has shown that xenon can protect against both glutamate and oxygen glucose deprivation induced excitotoxicity (Wilhelm et al., 2002; Ma et al., 2003a). At anesthetic concentrations in vivo (75%), xenon has been shown to dose-dependently protect against excitotoxic insults with the same neuroprotective efficacy as MK801 (Ma et al., 2002). Additionally, the same experiments showed that even at this relatively high dose of xenon, there is no evidence of any neurotoxicity in the posterior cingulate or retrosplenial corticies. More recent studies have shown that xenon based anesthesia provides a functional neurological improvement in rats subjected to cardiopulmonary bypass (Ma et al., 2003b).

Electrophysiology experiments have characterised xenon as a potent post-synaptic (De Sousa et al., 2000) non-competitive inhibitor of NMDA receptors with little or no GABA mediated effects (Franks et al., 1998). Although this may be the mechanism behind the anesthetic effect, it is almost certain that xenon has other sites of action that are yet to be elucidated. This theory is supported by xenon's ability to act in opposition to other NMDA receptor antagonists, by attenuating their neurotoxic effects (Nagata et al., 2001).

To date there is relatively little data on the effects of xenon on the neonate. In terms of safety, studies have shown that xenon, in contrast to $N_2O$, does not interfere with PKC control of the extending axon in vitro (Fukura et al., 2000) or exhibit teratogenic properties in vivo (Lane et al., 1980). Concerning efficacy, xenon has been shown to be an effective analgesic agent in neonatal rats (Ma et al., 2004).

The In Vivo Rat Model of Anesthesia: Protocol

Preliminary experiments suggested that 75% xenon+0.75% isoflurane was too high a dose for neonatal rat pups—inducing apnoea in 100% of test subjects within 10 min. This is supported by existing data that xenon is a more potent anesthetic and analgesic than nitrous oxide (Sanders et al., 2003). 60% xenon+0.75% isoflurane was substituted as a concentration more likely to be of equivalent MAC with 75% nitrous+0.75% isoflurane.

Sprague-Dawley are an inbred strain which display certain phenotypic differences to rats used in earlier studies. Specifically, when attempting to replicate previously used high-dose regimens (Jevtovic-Todorovic et al., 2003), e.g. 75% $N_2O$+1% isoflurane+6 mg/kg midazolam, the rats exhibited a high degree of susceptibility—mortality rates would have been 100% in the absence of intervention to end anesthetic exposure. Thus, gas concentrations for each group had to be adapted to induce a state of anesthesia without causing apnoea.

Characterisation of Neurodegeneration

The Cupric-Silver technique (DeOlmos Silver Staining) has repeatedly been shown to be excellent for highlighting the density and distribution of neurodegeneration (Beltramino et al., 1993; Jevtovic-Todorovic et al., 2003). The process highlights argyrophilia (a generalised CNS response to injury (O'Callaghan and Jensen, 1992)) to reveal cumulative neurodegeneration, so issues surrounding the small timeframe of marker expression, as in other techniques identifying gene products and enzyme activation, do not apply (DeOlmos and Ingram, 1971).

Caspase-3 immunohistochemistry appeared to be acting as a suitable marker of neuronal apoptosis. As a cytoplasmic enzyme, activated caspase-3 stained cells were stained in their entirety, hence making quantification relatively straightforward.

At the end of the apoptotic signalling cascade, caspase-9 activates caspase-3 (a cysteine protease), and thus caspase-3 is a marker of those cells that are downstream of the apoptotic commitment point. While broadly paralleling silver staining, caspase-3 immunohistochemistry is superior for both quantification purposes and characterisation of physiological cell death (Olney et al., 2002b).

C-Fos is one of the immediate early genes that has a role in linking cytoplasmic events to nuclear gene transcription (Walton et al., 1998). As a regulator of gene expression, c-Fos indicates a state of neuronal activation, a result of several possible different external stimuli, including apoptotic cell death (Dragunow and Preston, 1995) and pain (reviewed in Duckhyun and Barr, 1995). C-Fos has previously been shown to be a sensitive marker of the neurotoxicity of NMDA receptor antagonists in adult rats (Ma et al., 2002) and is valid for assessment of NMDA receptor activation (Hasegawa et al., 1998). The c-Fos immunohistochemistry protocol (Ma et al., 2002), formed the entire basis of quantification in the spinal cord formalin tests, staining activated nuclei black.

Anesthetic-Induced Apoptosis

It can be deduced from existing data that the developing human brain, both in utero and the first years of life, undergoes a highly dynamic transformation from a fetal phenotype to one that resembles the adult phenotype. The hallmarks of this process are an extremely rapid turnover of synapses (as high as 20% per day (Okabe et al., 1999)) and a high level of background apoptosis, as neurones that fail to reach their synaptic targets are eliminated, presumably to preserve energy-efficiency (Hua and Smith, 2004). This study confirms that exposure to certain anesthetic agents during this critical stage of neurodevelopment (synaptogenesis) causes apoptosis in the developing brain. Experiments have demonstrated that exposure to isoflurane, a commonly used GABAergic inhalational agent, induces a 4-fold increase in the level of apoptosis in the cortex. Also, nitrous oxide (whilst not manifesting any neurodegenerative properties as an individual agent) exhibits its neurodegenerative potential by significantly enhancing isoflurane induced apoptosis to twelve times that seen in controls. Similar results were obtained from the hippocampus, where isoflurane and the isoflurane-nitrous oxide mixture increased the level of apoptosis (4-fold and 7-fold respectively).

The hippocampus, a specialised fold of cortical tissue forming part of the limbic system, has an important function in memory formation (Aggleton and Brown, 1999).

Neurones in the hippocampus have the ability to exhibit the phenomenon know as 'long term potentiation' (LTP), whereby synaptic efficacy is progressively strengthened by specific patterns of neural activity. This process is thought to be the basis of memory at the cellular level. Classically, hippocampal processing takes place in both the hippocampus and the parahippocampal gyms (subiculum), before being projected to the fornix. Given the extent of neuronal injury in the hippocampus and subiculum, it is not surprising that rats exposed to high levels of anesthetics as neonates show signs of learning deficits as adults (Jevtovic-Todorovic et al., 2003) backed up by the finding of LTP suppression in the same study.

Given the clear implications for paediatric anesthesia, much work is underway to characterise the mechanism behind this process. Activation of both the GABA receptor and the NMDA receptor are known to influence survival signalling for neurones (Brunet et al., 2001; Bittigau et al., 2002). With this in mind, the ethanol-intoxicated mouse has formed the basis of an animal model for the study of this process. Although caspase-3 is an excellent marker of apoptotic cells, its position as the end-effector of a highly divergent death signalling cascade offers little insight into the mechanism of apoptosis. Caspase-3 activation is a common step to both the extrinsic 'death receptor' mediated and intrinsic 'mitochondrial' pathways of apoptosis (Green, 2000).

Young et al. hoped to narrow down the search to a single pathway with a series of elegant experiments. A combination of dual immunohistochemistry-immunofluorescence, Western blot analysis, and knock-out mice was used to highlight pathway-specific components, among them Bax and cytochrome c (intrinsic), and caspase-8 (extrinsic) (Young et al., 2003). It was found that whilst wild type mice treated with ethanol exhibited the characteristic pattern of ethanol-induced apoptosis, homozygous Bax-knockout mice given the same treatment showed virtually no sign of apoptosis at all; indeed, the level of apoptosis was lower than that seen in the physiological cell death of controls0. Additionally, they established that caspase-8 activation does not take place. This clearly implicates the intrinsic apoptosis pathway in anesthetic-induced apoptosis. This pathway, centred around the mitochondria, is controlled by an assortment of pro- and anti-apoptotic mediators in the cytosol of neurones. In the context of developing neurones, $Bcl-X_L$ (a member of the Bcl-2 family) is principally anti-apoptotic, whereas Bax is pro-apoptotic (Yuan and Yanker, 2000). Young et al. hypothesised that ethanol, a dual NMDA receptor antagonist and GABAergic agent, has the ability to dislodge Bax from the mitochondrial membrane, where is usually stored in an inactive state. Once in the cytosol, Bax (if unchecked by $Bcl-X_L$) becomes part of an active complex, which is in turn capable of returning to, and disrupting, the mitochondrial membrane (Korsmeyer et al., 2002). The subsequent translocation of mitochondrial contents (specifically cytochrome c—ordinarily part of cellular energy production) into the cytosol is thought to produce an extremely powerful pro-apoptotic signal. Cytosolic cytochrome c forms a complex with Apaf-1 and capsase-8, which then activates caspase-3, resulting in the initiation of further cascades, ultimately causing the characteristic cleavage of both cytoskeletal proteins and DNA (Dikranian et al., 2001). Of course, from this analysis it is not possible to identify the exact point at which anesthetics interact with this pathway. Also, individual classes of agents are capable of inducing apoptosis (e.g. isoflurane alone (Jevtovic-Todorovic et al., 2003) and ketamine alone (Ikonomidou et al., 1999)), so use of a dual GABAergic agent and NMDA receptor antagonist does not distinguish potential differences between the two receptor interactions, although the ensuing intracellular cascades may converge downstream (Brunet et al., 2001; Bittigau et al., 2002). It is entirely possible that isoflurane and or nitrous oxide can dysregulate the intraclellular Bax/Bcl-2 ratio, perhaps by disrupting intracellular calcium trafficking.

Use of Xenon During Synaptogenesis: Xenon as an Individual Agent

The blood brain barrier effectively blocks the translocation of many water-soluble substances from the blood to the CNS. It achieves this via a network of tight-junctions, overlapping astrocyte cover, and the relative absence of transport mechanisms. However, none of these measures are an effective obstacle to xenon, a small and apolar atom, which can rapidly attain anesthetic concentrations in the brain (Sanders et al., 2003). Once at the synapse, xenon is thought to produce its anesthetic effect through non-competitive blockade of the NMDA receptor, albeit by a mechanism that does not produce a typical open-channel block.

The results of the present study show that inducing a state of anesthesia with 75% xenon does not cause apoptotic neurodegeneration in the neonatal brain. Studies have conclusively proved that blockade of the NMDA receptor is a key element of this process (possibly via deprivation of electrical or trophic stimulation), with detrimental effects produced with use of MK801, ketamine, phencyclidine (PCP), and carboxypiperazin-4-yl-propyl-1-phosphonic acid (CCP) (Ikonomidou et al., 1999). It is therefore peculiar that xenon, a potent NMDA receptor antagonist (with 75% xenon equivalent to MK801 in some contexts (Ma et al., 2002)), does not induce similar apoptotic neurodegeneration. In light of the volume of biologically plausible evidence pertaining to lack of trophic stimulation causing apoptosis during NMDA receptor blockade (reviewed in Haberny et al., 2002), it is tempting to suggest that xenon has a novel anti-apoptotic property, mediated by an as-yet undefined target (which could be membranous, cytoplasmic, mitochondrial or nuclear given xenon's unusual pharmacodynamic and pharmacokinetic properties). Whilst at least in theory xenon's unusual block of NMDA receptors could be responsible (e.g. via an NMDA receptor subunit that has a different distribution or level of expression in the neonate such as NR2B or NR2D, or even a preferential effect at extra-synaptic NMDA receptors (Hardingham et al., 2002)), xenon's capacity to diametrically oppose NMDA receptor antagonist mediated neurotoxicity suggests that there are other systems involved (Nagata et al., 2001). It is therefore possible that as an NMDA receptor antagonist, xenon could be inducing a degree of pro-apoptotic signalling via an intracellular signalling cascade, whilst the theoretical anti-apoptotic action simultaneously disrupts the very same cascade at a downstream position (and thus also blocking isoflurane-induced signalling).

Use of Xenon During Synaptogenesis: Xenon in Combination with Isoflurane

In this study we demonstrated that concomitant administration of 60% xenon can inhibit 0.75% isoflurane-induced apoptosis 4-fold, to a level not statistically different from controls exposed to air. This leads to the hypothesis that xenon has an anti-apoptotic effect within the framework of pharmacologically-induced apoptosis.

One well defined unique feature of xenon is its lack of effect at GABA receptors; it is this attribute which may underpin some of xenon's atypical effects on the CNS. Consequently it is reasonably safe to rule out any direct antagonism of isoflurane's action at the GABA receptor. The only remaining possibility is downstream disruption of the proposed isoflurane or nitrous oxide-induced apoptosis pathway, either by xenon directly, or by an indirect route possibly involving the modulation of other pathways e.g. dopaminergic (Ma et al., 2002).

Comparison between the data for xenon alone and xenon in combination with isoflurane suggests that xenon can lessen the degree of neuronal injury induced by isoflurane, whilst having minimal impact on the process of physiological cell death (seen in controls). This implies that xenon can disrupt pathological pro-apoptotic signalling. If xenon were to enhance the intrinsic 'survival' pathway (e.g. by upregulation of Bcl-$X_L$), then it would be reasonable to expect a reduction in the level of PCD on exposure to 75% xenon—which is clearly not the case. However, this is highly conjectural given the lack of understanding into the mechanisms involved; it is not currently known whether the apoptotic pathways hijacked by conventional anesthetics are identical to those controlling PCD. Answers may be found in an in-depth analysis of the different pathways involved in xenon's mechanism of action when compared to nitrous oxide (a gaseous NMDA receptor antagonist which is currently the closest comparable agent).

Clinical Implications

Given the price and MAC values of xenon, it is an economic necessity (even with the most advanced reclaim-recycling systems) as well as a clinical necessity for xenon anesthesia to be maintained with another agent. The present work with combinations of agents suggests that use of isoflurane, whilst inducing neuronal apoptosis as an individual agent, is suitable for this purpose in neonates.

Experiments have exposed xenon as potential treatment for anesthetic-induced apoptosis. Thus, the use of xenon in paediatric anesthesia (at economically feasible doses) could dramatically increase the safety of current general anesthetic protocols.

In summary, these data add credence to the safe and efficacious use of xenon in the neonate; xenon is currently the only known anesthetic shown not to induce neonatal neuronal apoptosis at clinically applicable doses. This opens the possibility of xenon-based anesthesia finding a cost-effective niche within paediatrics as a safe, potently analgesic, and potentially neuroprotective anesthetic agent.

Xenon/Sevoflurane Combinations

A further aspect of the invention relates to a combination comprising xenon and sevoflurane. Preferably, the combination is a synergistic combination.

Studies by the applicant have shown that surprisingly, combinations of xenon and sevoflurane at concentrations at which they are completely ineffective as individual agents, provide striking neuroprotection when combined and administered to a subject prior to hypoxic injury, i.e. xenon and sevoflurane in combination exhibit a surprising and unexpected synergistic protection against subsequent hypoxic injury.

Without wishing to be bound by theory, it is believed that the protective effect is anti-necrotic, rather than anti-apoptotic, i.e. the protective effect arises from the prevention of cell death by necrosis. Cell death can occur by apoptosis or necrosis. In the former, a stimulus initiates a cascade of events which ultimately leads to cell death; apoptosis is often referred to as "programmed cell death" and is a part of normal physiological development. In contrast, necrosis involves a stimulus which directly induces the death of the cell and is always a pathologic process.

Studies by the applicant have demonstrated that doses of xenon and sevoflurane that are ineffective when administered as individual agents work synergistically in combination, resulting in a greater reduction in LDH release than corresponding concentrations of the gases used alone. Experiments have shown that neither sevoflurane at 0.67%, nor xenon at 12.5%, produces a significant reduction in LDH release; thus using xenon or sevoflurane as individual preconditioning agents offers no significant protection from ischaemic damage. However when the two gases are used in combination as preconditioning agents, LDH release is significantly reduced. Further details of these experiments may be found in the accompanying examples.

In one preferred embodiment, the xenon is administered in a sub-therapeutically effective amount. In this context, the term "sub-therapeutically effective amount" means an amount which is lower than that typically required to produce anesthesia. Generally, an atmosphere of about 70% xenon is sufficient to induce or maintain anesthesia. Accordingly, a sub-therapeutic amount of xenon corresponds to less than about 70% xenon.

Likewise, in one preferred embodiment, the sevoflurane is administered in a sub-therapeutically effective amount. In this context, the term "sub-therapeutically effective amount" means an amount which is lower than that typically required to produce anesthesia. Generally, an atmosphere of about 2.5% sevoflurane is sufficient to maintain anesthesia. Accordingly, a sub-therapeutic amount of sevoflurane corresponds to less than about 2.5% sevoflurane.

Another aspect of the invention relates to a pharmaceutical composition comprising xenon and sevoflurane and a pharmaceutically acceptable diluent, excipient or carrier. Preferably, the pharmaceutical composition is an anesthetic formulation.

In one preferred embodiment, the formulation comprises from about 10 to about 30% xenon and from about 1 to about 5% sevoflurane (v/v), with the balance comprising oxygen or nitrogen, or a mixture thereof. More preferably, the formulation comprises from about 10 to about 20% xenon and from about 2 to about 4% sevoflurane, with the balance comprising oxygen or nitrogen, or a mixture thereof.

In one highly preferred embodiment of the invention, the formulation comprises about 12.5% xenon, about 0.67% sevoflurane, about 25% oxygen and the balance nitrogen.

A further aspect of the invention relates to an anesthetic formulation for preventing and/or alleviating one or more sevoflurane-induced neurological deficits in a subject, said formulation comprising xenon and a pharmaceutically acceptable diluent, excipient and/or carrier.

Another aspect of the invention relates to an anesthetic formulation for treating and/or alleviating and/or preventing sevoflurane-induced neurodegeneration in a subject, said formulation comprising xenon and a pharmaceutically acceptable diluent, excipient and/or carrier.

Yet another aspect of the invention relates to an anesthetic formulation for treating and/or alleviating and/or preventing sevoflurane-induced neuronal apoptosis in a subject, said formulation comprising xenon and a pharmaceutically acceptable diluent, excipient and/or carrier.

One aspect of the invention relates to the use of xenon and sevoflurane in the preparation of a medicament for providing neuroprotection and/or anesthesia and/or analgesia.

Another aspect of the invention relates to the use of xenon in the preparation of a medicament for providing neuroprotection and/or anesthesia and/or analgesia, wherein said medicament is for use in combination with sevoflurane.

Another aspect of the invention relates to the use of sevoflurane in the preparation of a medicament for providing neuroprotection and/or anesthesia and/or analgesia, wherein said medicament is for use in combination with xenon.

A further aspect of the invention relates to the use of (i) xenon, and (ii) sevoflurane, in the preparation of a medicament for alleviating and/or preventing sevoflurane-induced neuronal injury in a subject.

Another aspect of the invention relates to the use of xenon in the preparation of a medicament for preventing and/or alleviating one or more sevoflurane-induced neurological deficits in a subject. Preferably, the neurological deficit is associated with neuronal necrosis.

Another aspect of the invention relates to the use of xenon in the preparation of a medicament for treating and/or alleviating and/or preventing sevoflurane-induced neurodegeneration in a subject.

Another aspect of the invention relates to the use of xenon in the preparation of a medicament for treating and/or alleviating and/or preventing neuronal necrosis in a subject.

Another aspect of the invention relates to the use of xenon in the preparation of a medicament for treating and/or alleviating and/or preventing sevoflurane-induced neuronal apoptosis in a subject.

Another aspect of the invention relates to the use of xenon in the preparation of a medicament for preventing and/or alleviating sevoflurane-induced neuronal injury in a subject.

Another aspect of the invention relates to the use of xenon and sevoflurane in the preparation of a medicament for providing anesthesia in a subject, wherein the amount of xenon is sufficient to alleviate or prevent sevoflurane-induced neuronal injury.

Yet another aspect of the invention relates to the use of xenon in the preparation of a medicament for treating and/or alleviating and/or preventing neuronal necrosis, or a condition associated with neuronal necrosis.

Conditions associated with neuronal necrosis include, for example, ischaemic infarction and traumatic infarction.

A further aspect of the invention relates to a method of providing neuroprotection and/or anesthesia and/or analgesia in a subject, said method comprising administering to said subject a therapeutically effective amount of a combination of xenon and sevoflurane.

Preferably, the xenon and sevoflurane are administered prior to hypoxic-ischaemic injury, more preferably, at least 1 hour, more preferably at least 2 hours prior to hypoxic-ischaemic injury. In one particularly preferred embodiment, the xenon and sevoflurane are administered from about 2 to about 24 hours prior to hypoxic-ischaemic injury.

Preferably, the subject is a mammal, more preferably, a human.

For all aspects of the invention, preferably the subject is a neonatal subject.

In one preferred embodiment, the xenon and sevoflurane are administered to the neonatal subject by administering to the mother prior to and/or during labour, or prior to and/or during a cesarean section.

Another aspect of the invention relates to a method of preventing and/or alleviating sevoflurane-induced neurological deficits in a subject, said method comprising administering a therapeutically effective amount of xenon to said subject.

Another aspect of the invention relates to a method of treating and/or alleviating and/or preventing sevoflurane-induced neurodegeneration in a subject, said method comprising administering a therapeutically effective amount of xenon to said subject.

Another aspect of the invention relates to a method of treating and/or alleviating and/or preventing sevoflurane-induced neuronal apoptosis in a subject, said method comprising administering a therapeutically effective amount of xenon to said subject.

Another aspect of the invention relates to a method of treating and/or alleviating and/or preventing sevoflurane-induced neuronal necrosis in a subject, said method comprising administering a therapeutically effective amount of xenon to said subject.

Another aspect of the invention relates to a method of treating and/or alleviating and/or preventing sevoflurane-induced neuronal injury in a subject, said method comprising administering a therapeutically effective amount of xenon to said subject.

Yet another aspect of the invention relates to a method of preventing and/or alleviating sevoflurane-induced neuronal injury in a subject, said method comprising administering to said subject xenon and sevoflurane.

Another aspect of the invention relates to a method of providing anesthesia and/or analgesia in a subject, said method comprising administering xenon in combination with sevoflurane, wherein the amount of xenon is sufficient to alleviate and/or prevent sevoflurane-induced neuronal injury.

Another aspect of the invention relates to a method of treating and/or alleviating and/or preventing neuronal necrosis, or a condition associated with neuronal necrosis, in a subject, said method comprising administering a therapeutically effective amount of xenon to said subject.

Another aspect of the invention relates to a method of treating and/or alleviating and/or preventing neuronal necrosis, or a condition associated with neuronal necrosis, in a subject, said method comprising administering a therapeutically effective amount of xenon to said subject.

Yet another aspect of the invention relates to the use of xenon and isoflurane in the preparation of a medicament for use as a preconditioning agent for protecting against hypoxic injury.

As used throughout, the term "preconditioning agent" refers to a medicament that is capable of alleviating and/or preventing neuronal damage that may arise from a subsequent hypoxic injury. Typically, preconditioning agents may be administered prior to potentially injurious events such as invasive surgery, cardiopulmonary bypass (CPB), organ transplant, labour, prior to uterine implantation of fertilized embryo (as part of in vitro fertilization), neurovascular surgical procedures, brain tumour resections and the like. Preconditioning agents may also be administered after one or more injurious events where the subject may be at risk of subsequent further injurious events, for example, stroke patients.

Preferably, when used as a preconditioning agent, the xenon is administered prior to hypoxic-ischaemic injury, more preferably, at least 1 hour, more preferably at least 2 hours prior to hypoxic-ischaemic injury. In one particularly preferred embodiment, the the xenon is administered from about 2 to about 24 hours prior to hypoxic-ischaemic injury.

Yet another aspect of the invention relates to the use of xenon in the preparation of a medicament for use as a preconditioning agent for protecting against hypoxic injury, wherein said medicament is for use in combination with sevoflurane.

Yet another aspect of the invention relates to the use of sevoflurane in the preparation of a medicament for use as a preconditioning agent for protecting against hypoxic injury, wherein said medicament is for use in combination with xenon.

A further aspect of the invention relates to a method of protecting a subject from hypoxic injury, said method comprising administering to said subject a therapeutically effective amount of a combination of xenon and sevoflurane.

The present invention is further described by way of non-limiting example and with reference to the following figures wherein:

Rats were anesthetised for a period of 6 hrs (neurodegeneration experiments) or 105 min (formalin test). Once the brains were removed, sections were cut to include the region of interest: a coronal section −3.6 mm from the bregma (neurodegeneration experiments) or a transverse section of the lumbar enlargement of the spinal cord (formalin test). FIG. 1A: Diagram depicting a sagittal view through the neonatal rat brain, and the transverse slice used for counting. FIG. 1B: Diagram of a transverse section through the lumbar enlargement of the spinal cord of the neonatal rat—dotted lines represent boundaries of counting regions, taken from a previously used protocol (Duckhyun and Barr, 1995).

FIGS. 2A-2D show silver stained sections. DeOlmos silver staining was employed to determine potential areas of interest for immunohistochemistry. Rats were anesthetised with various gas combinations, had their brains removed, and sections cut for DeOlmos silver staining. Areas of non-specific neurodegeneration are stained black (×4 magnification). FIG. 2A: Photomicrograph of the cortex of a control animal, showing low silver uptake. FIG. 2B: Photomicrograph of the cortex of a rat exposed to 75% nitrous oxide+0.75% isoflurane, showing silver uptake in specific cortical layers. FIG. 2C: Photomicrograph of the hippocampus of a control animal, showing low silver uptake. FIG. 2D: Photomicrograph of the hippocampus of a rat exposed to 75% nitrous oxide+0.75% isoflurane, showing extensive silver uptake.

FIG. 3 shows hippocampal apoptotic neurodegeneration induced by exposure to anesthetics in neonatal rats: mean data. Apoptotic neurodegeneration induced in the cortex and hippocampus by mock anesthesia or exposure to anesthetics (75% nitrous oxide, 75% xenon, 0.75% isoflurane, 75% nitrous oxide+0.75% isoflurane or 75% xenon+0.75% isoflurane) as measured with caspase-3 immunostaining in the cortex of 7 day old neonatal rats. Mean data from cortex (mean±SD, n=3) from all treatment groups. $p<0.01$ vs air; *$p<0.001$ vs air. FIG. 3: Mean data from hippocampus (mean±SD, n=3) from all treatment groups. **$p<0.01$ vs air.

FIG. 4 shows cortical apoptotic neurodegeneration in neonatal rats exposed to individual anesthetic agents. Photomicrographs (×4 magnification) showing caspase-3 immunostaining of the cortex, highlighting cells destined for apoptosis (black staining). Photomicrographs (×4 magnification) correspond to gas exposure: air (A), 75% nitrous oxide (B), 75% xenon (C), or 0.75% isoflurane (D) for 6 hrs.

FIGS. 5A-5C show cortical apoptotic neurodegeneration in neonatal rats exposed to combinations of anesthetic agents. Photomicrographs (×4 magnification) comparing caspase-3 staining in the cortex of neonatal rats exposed to either 75% nitrous oxide+0.75% isoflurane (A), or 60% xenon+0.75% isoflurane (B) for 6 hrs. Despite the fact that both nitrous oxide and xenon are characterised as NMDA receptor antagonists, they exhibit diametrically opposite properties when modulating isoflurane-induced apoptosis (enhancing and attenuating respectively). High power light microscopy (×20 magnification) confirmed that entire neurones where being stained, in keeping with caspase-3 being a cytoplasmic enzyme (C).

FIG. 6 shows hippocampal apoptotic neurodegeneration induced by exposure to anesthetics in neonatal rats. Following a 6 hr gas exposure, caspase-3 immunostaining of the hippocampus was performed to highlight cells destined for apoptosis (black staining). Photomicrographs (at ×4 magnification) correspond to gas exposure: air (A), 75% nitrous oxide (B), 75% xenon (C), 0.75% isoflurane (D), 75% nitrous oxide+0.75% isoflurane (E), and 60% xenon+0.75% isoflurane (F).

FIGS. 7A-7C show the results from formalin testing. The analgesic potential of (75% nitrous oxide+0.75% isoflurane) was compared to (60% xenon+0.75% isoflurane) using a formalin test to quantify the nociceptive response to a formalin injection to the left-hind paw via c-Fos expression in the spinal cord. FIG. 7A: Mean data (mean±SD, n=3) from all treatment groups. ***$p<0.001$ vs formalin injected controls; ⁺$p<0.05$ vs $N_2O$+Iso. FIG. 7B: Photomicrograph of spinal cord slice for 75% nitrous oxide+0.75% isoflurane. FIG. 7C: Photomicrograph of spinal cord slice for 60% xenon+0.75% isoflurane.

EXAMPLES

Materials and Methods

This study conforms to the UK Animals (Scientific Procedures) Act of 1986 and the study protocol has Home Office approval.

Example 1

Exposure to Anesthetic Gases

Animals 7 day old Sprague-Dawley rat pups were placed in individual wells of a custom-built anesthetic chamber, and randomised to groups A-F to receive one of 6 gas combinations for 6 hours. Previous work has established that NMDA receptor antagonists have their maximal neurodegenerative affect 7 days after birth (Ikonomidou et al., 1999).

Gas Delivery

Group B received 75% nitrous oxide and 25% oxygen as delivered by a calibrated anesthetic machine, whereas group C received 75% xenon along with 25% oxygen through a customised anesthetic machine modified for xenon delivery (Ohmeda, modified by Air Products, Surrey, UK). Group D were exposed to 25% oxygen along with 0.75% isoflurane. The remaining 2 groups were exposed to combinations of gases—namely 25% oxygen+75% nitrous oxide+0.75% isoflurane (group E) and 25% oxygen+60% xenon+15% nitrogen+0.75% isoflurane (group F). The high cost of xenon precludes its use in an open-circuit, consequently group C and group F received gases using a closed-circuit system, whereas gases for all other groups were delivered in a high-flow open-circuit.

Monitoring

All rats were kept normothermic throughout using a water bath combined with a thermostat. Gas concentrations were monitored with a S/5 spirometry module (Datex-Ohmeda, Bradford, UK), and the rats themselves were regularly checked for signs of respiratory distress. Given the inert chemical characteristics of gaseous xenon, a special 439XE monitor (Air Products, Surrey, UK), was used to verify the delivery of anesthetic concentrations of xenon, based on radiofrequency analysis.

Tissue Perfusion, Harvesting, and Fixation

Rats destined for immunohistochemistry were sacrificed with 100 mg kg$^{-1}$ sodium pentobarbital IP immediately post-anesthesia, whereas those rats for DeOlmos silver staining were allowed to recover for 18 hrs before undergoing the same procedure. A thoracotomy was performed, and the aorta cannulated via a needle inserted into the apex of the heart. The pup was then perfused with 10 ml of 1% heparin solution, with the excess solution leaving through an incision in the right atrium. To fix the tissues, 20 ml of 4% paraformaldehyde in 0.1M phosphate buffer was injected by the same transcardial route. The whole brain was then removed and allowed to fix in paraformaldehyde perfusate and refrigerated at 4° C. 24 hours later, the brains were transferred to a solution of 30% sucrose with phosphate buffer and 1% sodium azide, and were kept refrigerated until the brains sank (approximately 48 hours).

Sectioning

Figure 1A:
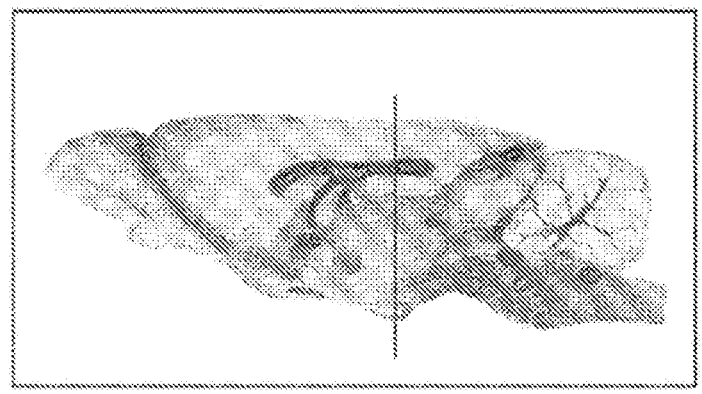
Figure 1B:
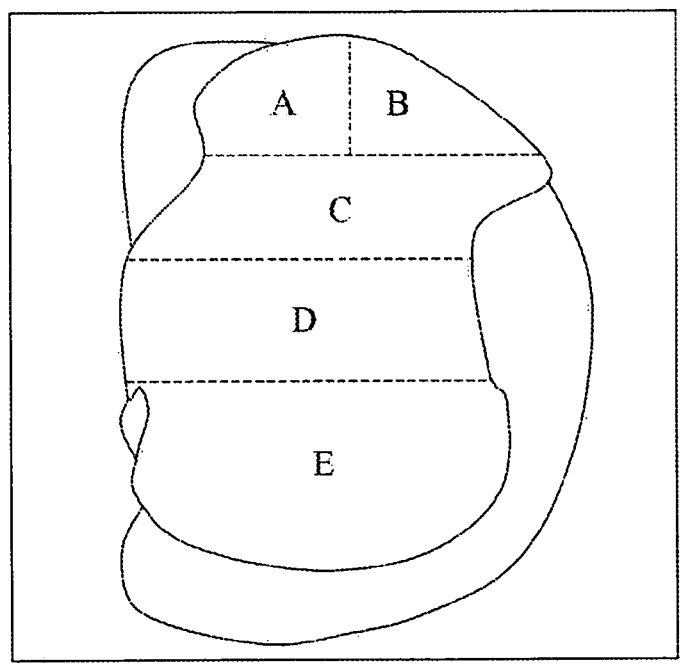

Once processed, a block was cut to safely include the area of interest—a coronal section −3.6 mm from the bregma (FIG. 1B). The blocks were then embedded and frozen into O.C.T. solution. The block was then cut coronally into approximately 120 slices, each 30 μm thick, with a cryostat (Bright Instrument Company Ltd., Huntingdon, UK). The cut sections were transferred to a 6 well plate containing phosphate buffered saline (PBS).

Staining Protocols

DeOlmos Silver Staining

DeOlmos silver staining was carried out according to an established protocol (DeOlmos and Ingram, 1971). The floating sections were mounted onto adhesive polysine slides, washed in distilled water, and then incubated in a copper-silver mixture (1000 ml 2.5% silver nitrate, 15 ml 0.5% cupric nitrate, 40 ml of pyridine and 80 ml of 95% ethyl alcohol). After 4 days the sections were removed, treated with 100% acetone for 5 min, and then transferred to freshly prepared ammoniacal silver nitrate stock (300 ml of distilled water, 200 ml of 0.36% NaOH, 90 ml concentrated ammonium hydroxide and 10 ml of 20% silver nitrate) for 15 min. Immediately following the ammoniacal silver nitrate, the slides were placed in a reducer solution made of 24 ml 10% non-neutralised formalin, 14 ml of 1% citric acid, 200 ml of 100% ethanol and 1762 ml of distilled water for 2 min. To complete processing, the sections had their background stained yellow with 0.5% potassium ferricyanide, were bleached for 1 min in 1% sodium thiosulphate and then washed in distilled water. They were then gently dehydrated in 70%, 90% and 100% ethanol. The ethanol was then cleared with two 5 min exposures to 100% xylene. While still wet with xylene, the slides had 2 drops of styrolite coverslip media (BDH, Poole, UK) added, and were then coverslipped. Having tapped out the air bubbles, the slides were allowed to dry overnight before light microscopy.

Caspase-3 Immunohistochemistry

A random well from each cut block, each containing around 20 representative slices of the total block, was transferred to a marked silk-bottomed well using a 3 ml Pasteur pipette. The sections were then washed in 5 ml of PBS for 5 min on a shaker set at 75 rpm. This washing procedure was repeated twice more, replacing the PBS each time. To quench the sections, they were incubated at room temperature on a shaker for 30 min in a solution comprising 35 ml methanol, 15 ml of PBS and 500 μl of stock 30% $H_2O_2$.

The quenching solution was then removed, and the sections washed three times in PBS. Sections were blocked for 60 min at room temperature with 50 ml of PBST (PBS containing 0.5% Triton-X (Promega Corporation, Madison, Wis.)), and 1500 μl of normal goat serum (NGS) (Vector Laboratories Inc., Burlingame, Calif.). For incubation with the primary antibody, the sections were kept overnight at 4° C. on a shaker set at 50 rpm in a solution made up of 16 μl (1:1500) rabbit anti-cleaved caspase-3 antibody (New England Biolabs, Hertfordshire, UK), 50 ml of PBST and 500 μl of NGS. The next day the sections were washed 3 times in PBST and then incubated with the secondary antibody for 60 min in a solution made up with 50 ml of PBST, 750 μl of NGS and 250 μl of goat anti-rabbit IgG antibody (Chemicon International, Temecula, Calif.). Following a further 3 washes in PBST, the sections were incubated in freshly prepared ABC solution from a Vectastain ABC kit (Vector Laboratories Inc., Burlingame, Calif.) for 60 min. The ABC solution was then washed off with 3 changes of PBS, whilst fresh 3,3'-diaminobenzidine (DAB) solution was prepared, which included distilled water, buffer, DAB stock, $H_2O_2$ and nickel solution from a peroxidase substrate kit (Vector Laboratories Inc. Burlingame, Calif.). The slices were immersed in DAB solution for 4 min at room temperature, immediately washed 3 times with PBS to end staining, and then washed 3 times with distilled water.

To mount the sections onto microscope slides, the well contents were floated into distilled water and the individual sections transferred to superfrost slides using a fine paintbrush. Once mounted, slides were allowed to dry overnight. To complete processing of the slides, the samples slides were then dehydrated, cleared and coverslipped as for the DeOlmos silver staining.

C-Fos Immunohistochemistry

The c-Fos immunohistochemistry was performed in parallel with the caspase-3 immunohistochemistry with only three changes to the protocol. Whereas NGS was used in the caspase-3 protocol, normal donkey serum (NDS) (Chemicon International, Temecula, Calif.) was used for the c-Fos wells. The primary antibody used was 20 µl (1:2500) of goat anti-c-Fos antibody (Santa Cruz Biotechnology, Santa Cruz, Calif.), and the secondary antibody was 250 µl of donkey anti-goat antibody (Chemicon International, Temecula, Calif.). All other stages of c-Fos immunostaining were identical to caspase-3 immunohistochemistry protocol.

Quantification

The number of degenerating or activated neurones was determined by counting the number of DAB stained (black) cells in a coronal section of one hemisphere around −36 mm from the bregma visualised on a BX-60 light microscope (Olympus, Southall, UK) and example photomicrographs were taken with a Axiocam digital camera (Zeiss, Göttingen, Germany). Data was collected for both the cortex and the hippocampus across 3 slices, after which the mean number of degenerating neurones was calculated. Those sections stained with the silver staining method were photographed down the microscope without any formal counting.

Data Analysis

All results are expressed as mean±standard deviation. Statistical analysis comprised a parametric repeated measures analysis of variance of means followed by a Newman-Keuls test for multiple comparisons across groups A-F. A P value of <0.05 was considered statistically significant.

Formalin Testing

Figure 1C:
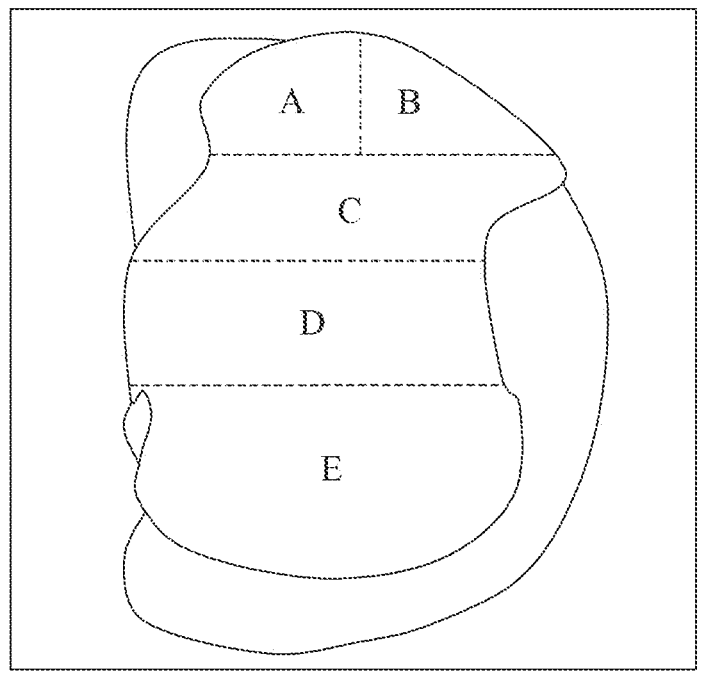
Figure 2A:
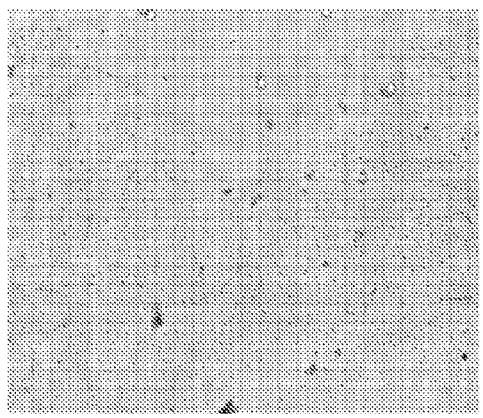
Figure 2B:
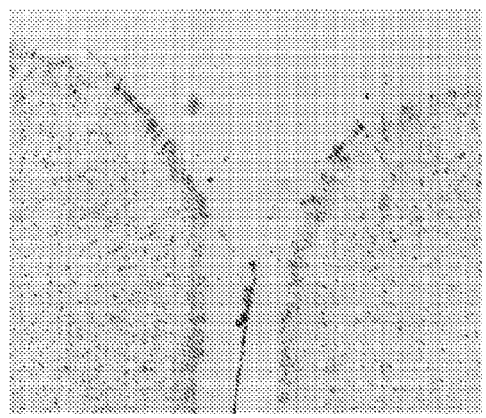
Figure 2C:
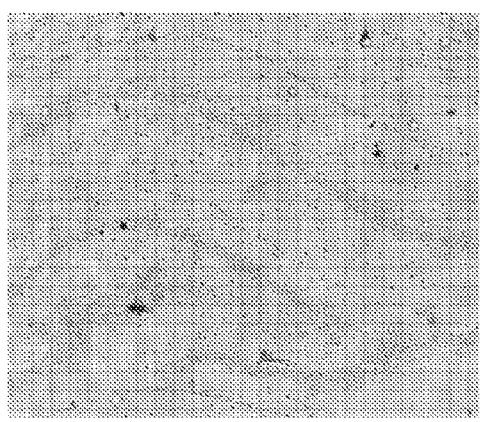
Figure 2D:
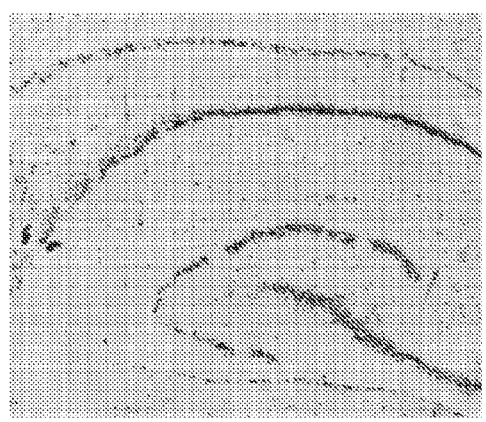

Formalin testing was carried out according to an established protocol (Ma et al., 2004) to compare group E with group F. Rats from one litter were randomised to one of 4 groups to receive different injections and gases: air+formalin, air+saline, 60% xenon+0.75% isoflurane+formalin or 75% nitrous oxide+0.75% isoflurane+formalin. All rats were exposed to the respective gas mixture for 15 min, and then had the left-hind paw injected with either formalin (10 µl of 5% formalin) or an equivalent volume of saline. Following a further 90 min of gas exposure, the animals/spinal cord samples were sacrificed, perfused and fixed as in the main study. Out of the whole spinal cord, a block was cut, comprising the lumbar enlargement. 30 µm transverse sections were cut on a cryostat, and the sections processed for c-Fos immunohistochemistry. After staining, 3 sections exhibiting maximal c-Fos expression were selected and photographed from each group, and the spinal cord divided into regions as reported previously (FIG. 1C) (Duckhyuan and Barr, 1995). The mean number of c-Fos positive cells was then calculated by region for statistical analysis.

Results

DeOlmos Silver Staining

As a non-specific marker of regions undergoing neurodegeneration, the DeOlmos silver staining particularly highlighted both the hippocampus and specific cortical layers. These areas showed extensive silver uptake, denoted by black staining in sections exposed to anesthetics, as opposed to controls subjected to mock anesthesia where uptake was minimal (FIG. 2).

Caspase-3 Immunohistochemistry

Cortical Activated Caspase-3

Figure 4:
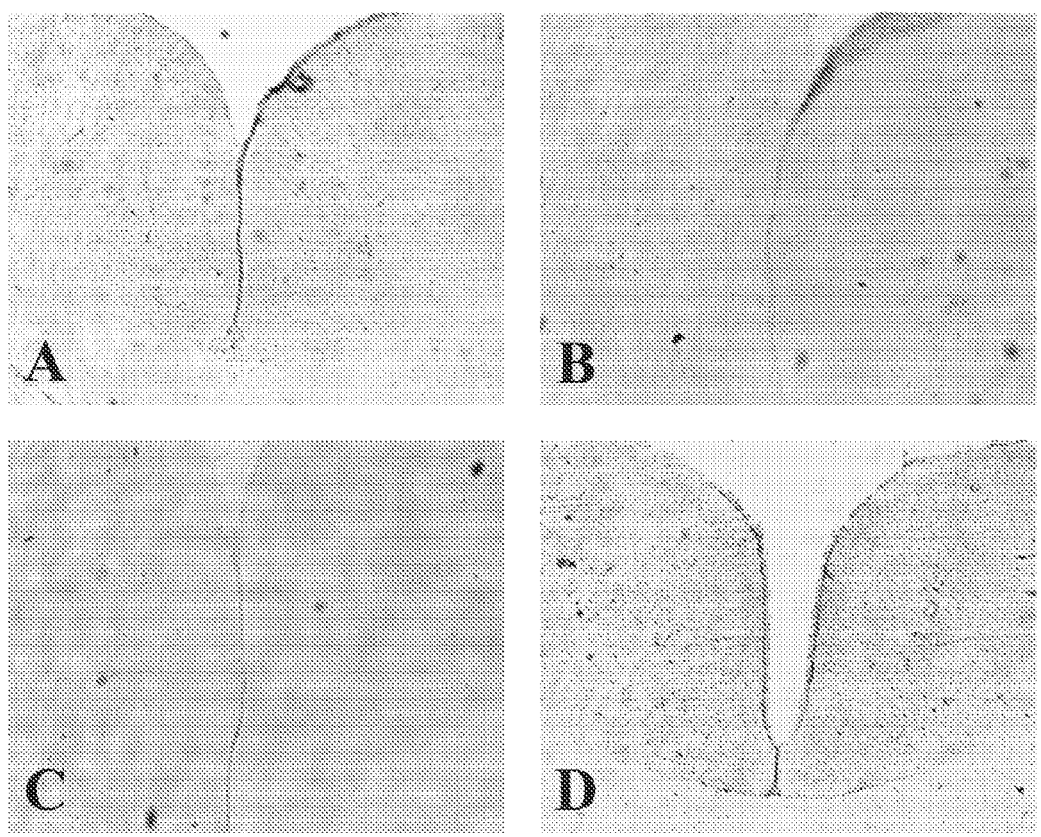

Neuronal cells exhibiting caspase-3 activation were readily distinguishable from the background as black cell body and axonal staining. The staining established the level of background level of cortical capsase-3 activation in rats exposed to air as 19.3±6.4 (mean±SD), n=4. As individual agents, neither 75% $N_2O$ nor 75% xenon induce a significant increase in caspase-3 positive cells (22.5±5.9, n=3 and 19.7±9.6, n=3 respectively; p>0.05 vs air) whereas administration of 0.75% isoflurane alone produced a moderate level of activated caspase-3 staining (76.5±11.4, n=5; p<0.01 vs air) (FIG. 4).

Figure 5A:
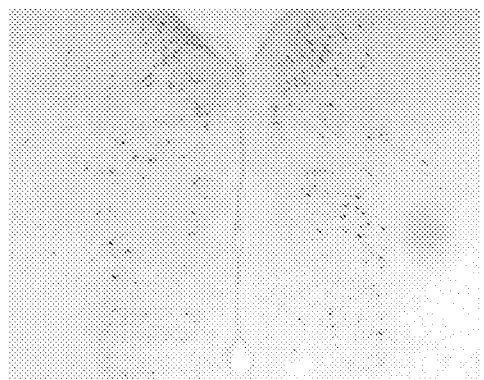
Figure 5B:
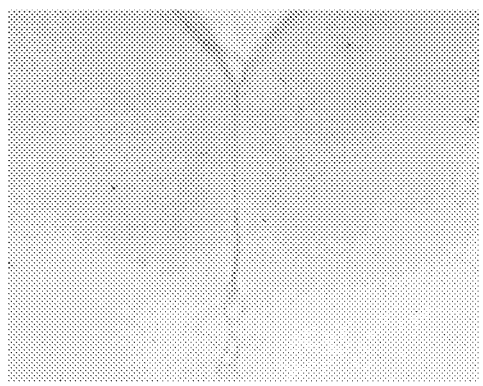
Figure 5C:
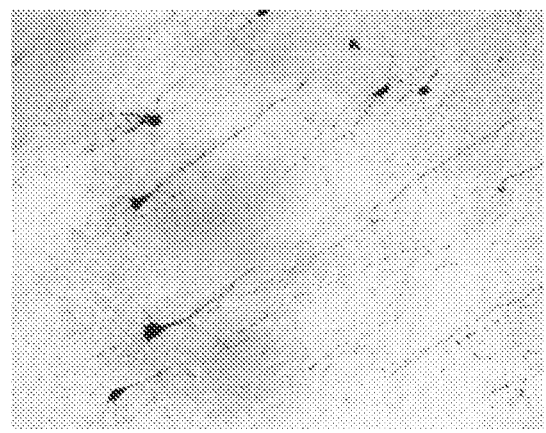

When combined with 0.75% isoflurane, 75% $N_2O$ considerably enhances isoflurane-induced apoptosis (232.0±19.9, n=6; p<0.001 vs air) while 60% xenon reduces the injury (26.7±3.9, n=4; p>0.05 vs air) (FIG. 5).

Hippocampal Activated Caspase-3

Figure 3:
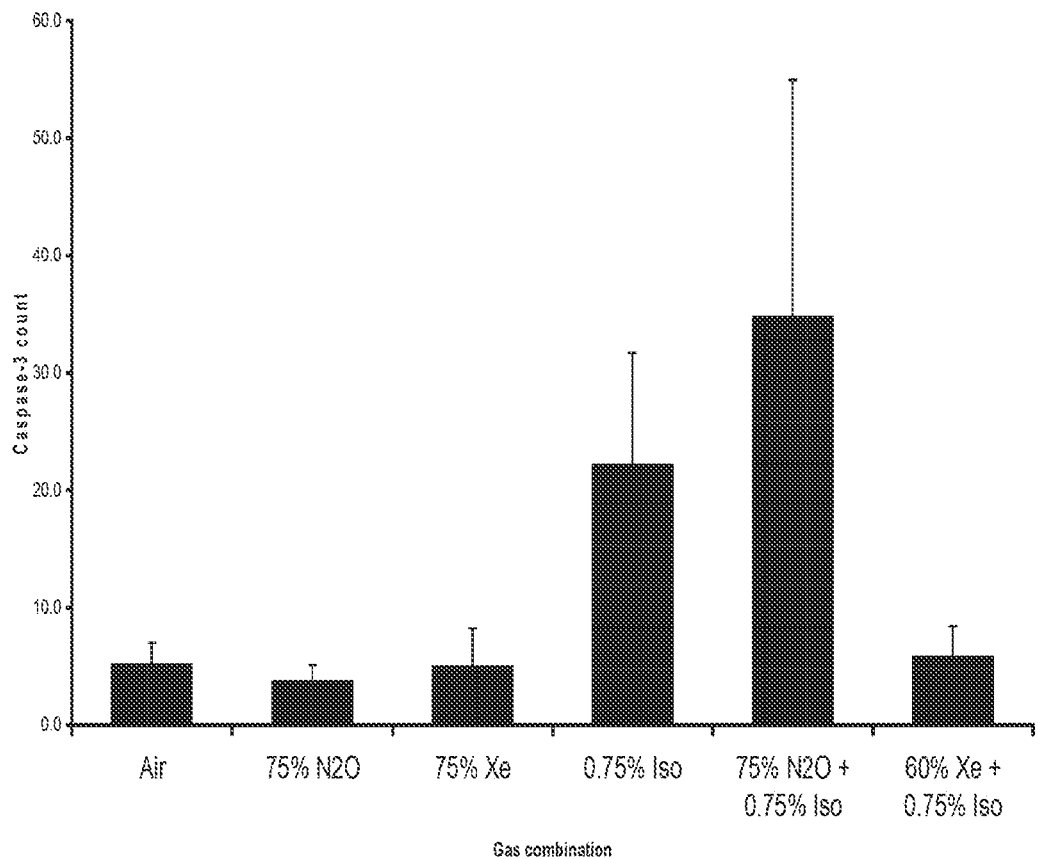
Figure 6:
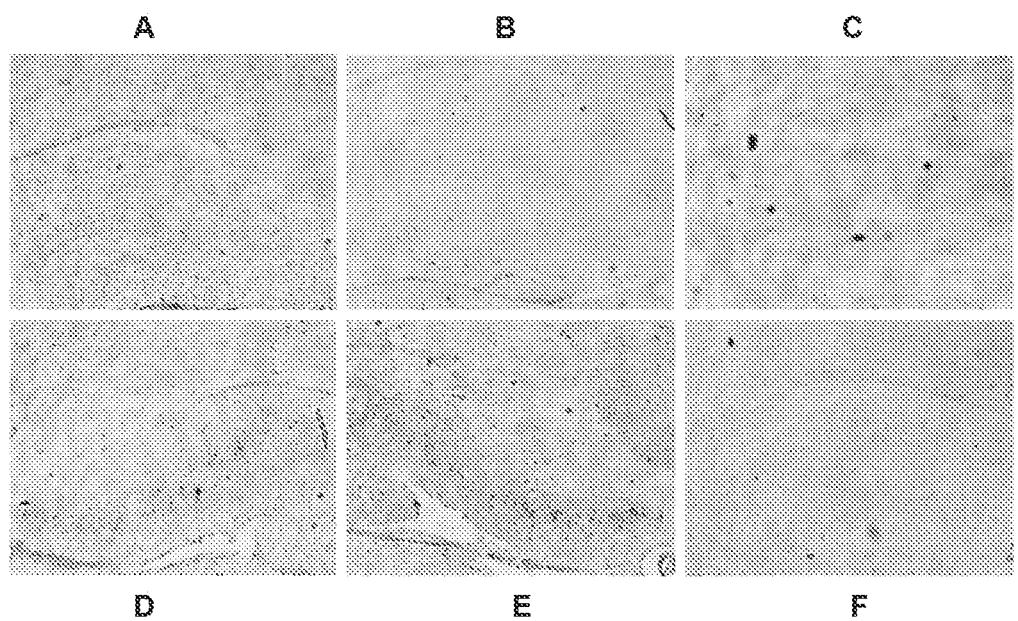

Neither 75% $N_2O$ nor 75% xenon exhibited a significant increase in caspase-3 positive cells above baseline (3.7±1.4 and 5.0±3.2 respectively vs 5.2±1.8 in controls; p>0.05) (FIG. 3). In contrast, 0.75% isoflurane alone significantly increases the number of degenerating neurones (22.1±9.6; p<0.01 vs air), as did the combination of 0.75% isoflurane and 75% $N_2O$ (34.8±20.2; p<0.01 vs air) (FIG. 6). Dual administration of 60% xenon with 0.75% isoflurane reduced the degree of neuronal injury to 5.8±2.6; p=<0.05 vs air.

Spinal Cord C-Fos Expression (Formalin Test)

Figure 7A:
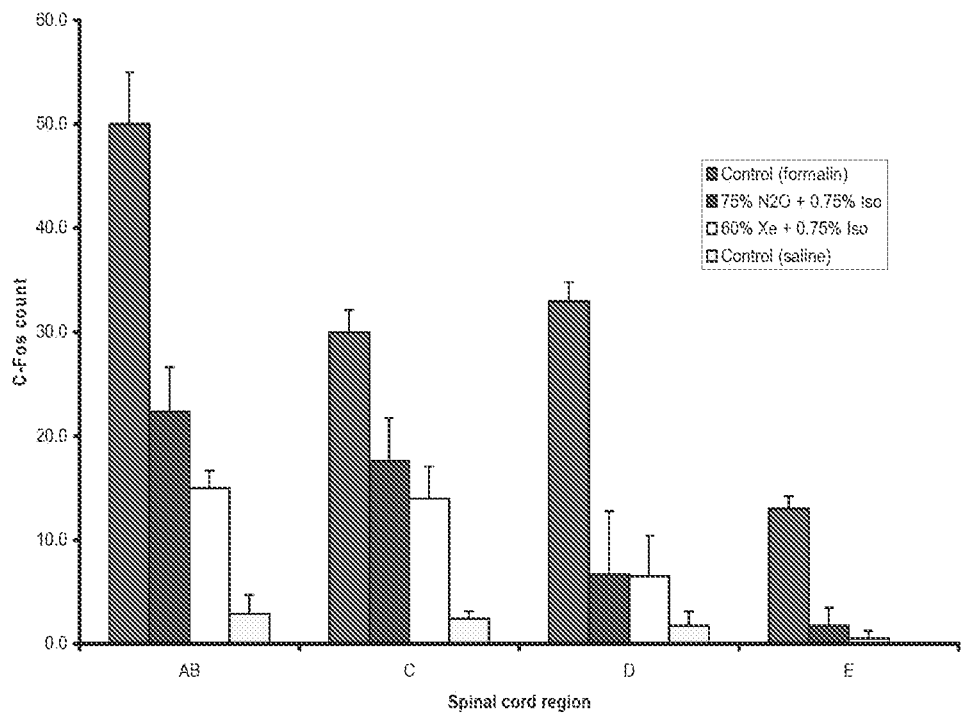
Figure 7B:
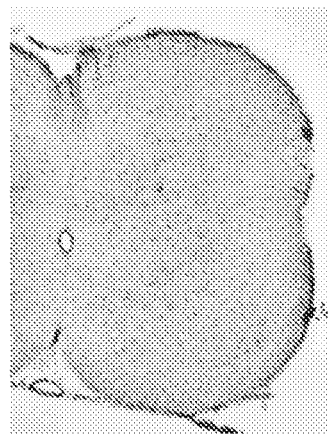
Figure 7C:

Both gas combinations (75% $N_2O$+0.75% isoflurane and 60% xenon+0.75% isoflurane) exhibited an analgesic effect by suppressing c-Fos expression in all regions of the spinal cord vs formalin-injected positive controls (p<0.001) (FIG. 7). In laminae A/B, where c-Fos expression was maximal, the xenon combination conferred a greater analgesic effect than that induced by the nitrous combination (15.0±1.7 vs 22.3±4.3 respectively; p<0.05).

Example 2

Methods

Neuronal Glial Co-Culture

Whole cerebral neocortices (devoid of the hippocampus, basal ganglia and meninges) were obtained from early post natal (1-2 day old) pups of BALB/c mice. The pups were anaesthetised with isoflurane and then decapitated with the heads placed immediately into 4° C. HSG solution, an isotonic, high sucrose glucose solution made primarily from Hank's balanced salt solution (HBSS, GibroBRL) enhanced with $NaHCO_3$ (0.04 M), sucrose (0.2 M) and D-Glucose (0.3 M) also containing antibiotic-anti-mycotic solution (AAS, GibroBRL). Throughout the micro dissection process, brain tissues were kept in 4° C. HSG solution.

The brain tissue was then immersed in 0.25% trypsin and was placed in a shaking air chamber for 50 minutes at 37° C. filled with 5% $CO_2$ and 95% room air. DNase was then added to the mixture and placed back into the shaking air chamber for a further 15 minutes. The mixture was then centrifuged at 1600 rpm for 10 minutes at 4° C. and the supernatant was carefully discarded. The cells were then resuspended and then plated at a density of $6.25 \times 10^4$ cells/cm$^2$ on 24-multiwell plates (Costar, Cambridge, Mass.) and cultured in a medium consisting of Eagle's minimum essential medium augmented with 20 mM glucose, 26 mM $NaHCO_3$, 10% foetal bovine serum, 10% heat-inactivated horse serum, AAS (Gibco, Paisley, UK), 2 mM glutamine (Sigma, Poole, UK) and 10 ng/ml murine epidermal growth factor (EGF) (GibcoBRL). Glial cells reached confluence about one week after plating.

Using a similar procedure cortical neuronal cells were obtained from fetal BALB/c mice at 14-16 days of gestation and plated at a density of $1.25 \times 10^5$ cells per $cm^2$ on the confluent monolayer of glial cells derived from the corresponding genetic strain. Neuronal cells reached confluence 10 days after plating.

Pure Neuronal Culture

Neuronal cells were harvested from 19 day old embryonic mice by cesarean section for pregnant BALB/c mice. 6-9 mouse brains were removed from fetal mice and dissected to isolate whole cerebral neocortices devoid of the hippocampus, basal ganglia and meninges. Again throughout the micro dissection process, brain tissues were kept in 4° C. HSG solution. From here, a similar plating procedure described above was performed. The cells were plated at a density of $1.2 \times 10^5$ cells, per $cm^2$ on 24-multiwell plates (Cater, Cambridge, Mass.) and the cultures were maintained at 37° C. in a humidified 5% $CO_2$ environment. Neurobasal Media supplemented with B27, glutamine and AAS was used to resuspend the neuronal cells and as culture medium. For every 10 ml of Neurobasal Media, the following supplements were added: 200 µl B27, 100 µl antibiotic and 25 µl glutamine. Medium replacement for these cells was performed on day 2, 5 and 7 with pre-warmed 37° C. culture medium (Neurobasal Media, B27, Glutamine and AAS). On day 5 after neuronal plating, 100 µl/10 ml cytosine arabinoside (CA hydrochloride, Sigma) was added to the cell cultures to halt non-neuronal cell division. Neuronal cell cultures were ready to use on day 7.

Preconditioning

Cells were preconditioned using a purpose built 1.4 liter airtight, temperature controlled gas chambers. The chambers had inlet and outlet valves and an internal electric fan to ensure effective and continuous delivery of gases. Gas flow rate was 100 ml/min, and so chambers were flushed and allowed to equilibrate for 45 minutes before establishing a closed system. Cells were preconditioned for 2 hours inside the closed system with the appropriate gas concentrations using flow meters. Sevoflurane was delivered using a vaporiser (Datex-Ohmeda).

Preparation of gas impregnated solutions—Deoxygenated balanced salt solution (BSS) was made by bubbling 5% $CO_2$ and 95% $N_2$ through sintered gas bubblers into the BSS in a Drechsel bottle in a 37° C. incubator.

Oxygen Glucose Deprivation

To model ischaemic damage in the brain, neuronal cells were subjected to oxygen glucose deprivation. Twenty four hours after preconditioning cells, cultures were washed twice with HEPES buffer solution (120 mM NaCl, 5.4 mM KCL, 0.8 mM $MgCl_2$, 15 mM glucose and 20 mM HEPES, titrated to pH 7.4 using 1M NaOH). They were then washed once with pre-warmed deoxygenated BSS minus glucose (116 mM NaCl, 5.4 mM KCL, 0.8 mM $MgSO_4$, 1 mM $NaH_2PO_4$, 1.8 mM $CaCl_2$, 26 mM $NaHCO_3$) and then titrated to a pH of 7.4 using 2M HCl. The culture medium was then replaced with 600 µl of deoxygenated BSS and then immediately placed into a 37° C. air tight gas exposure chamber and left to equilibrate to an anaerobic environment consisting of 5% $CO_2$ and 95% $N_2$. The cells were exposed to this anoxic environment for 75 minutes. Oxygen glucose deprivation was terminated by removing the cultures from the gas chamber and changing the media; cultures destined for lactate dehydrogenase (LDH) assay were washed once and replaced with Eagle's minimal essential medium enhanced with 25 mM glucose and 38 mM $NaHCO_3$, whereas pure neuronal cultures for FACS were washed once and replaced with Neurobasal Media supplemented with B27, glutamine and AAS.

LDH Measurement

Figure 8:
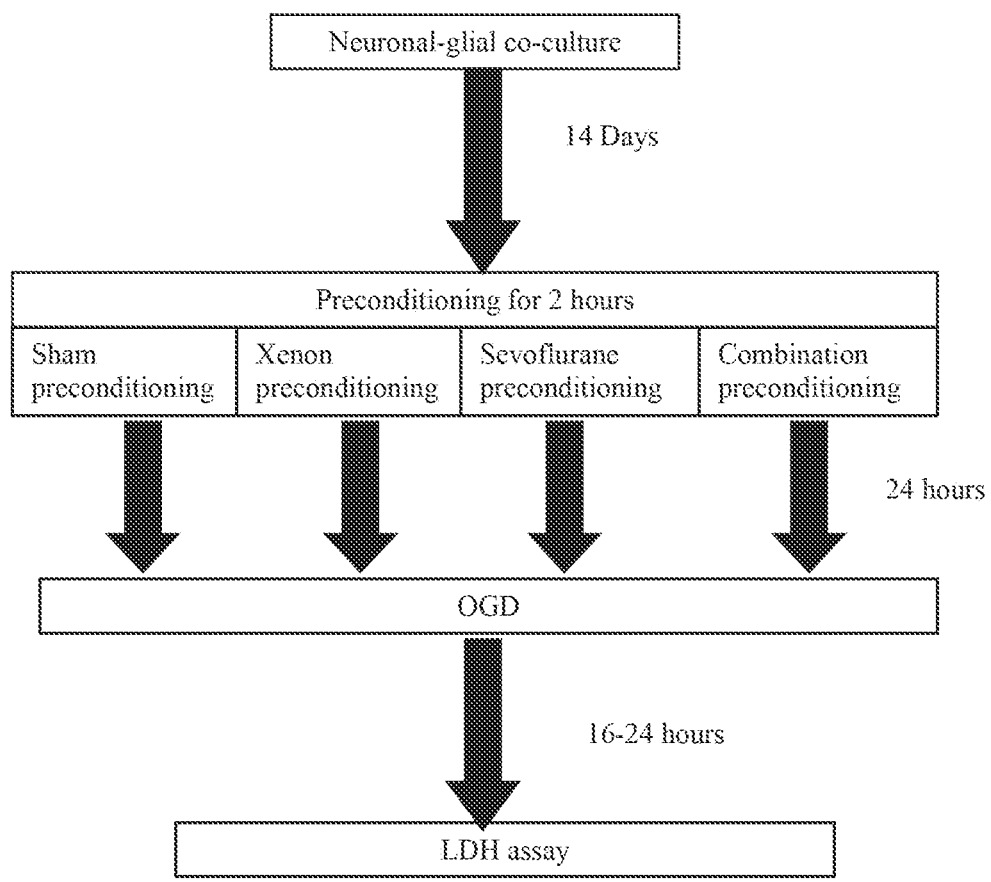
FIG. 8 shows the flow diagram of LDH assay protocol.

The amount of neuronal damage was assessed by the amount of LDH released into the culture medium, using a standardised colorimetric enzyme kit (Sigma, Poole, UK). This technique has been previously described (Wilhelm et al 2002). LDH assessment was performed 16 hours after oxygen glucose deprivation (FIG. 8).

FACS Assessment

Twenty fours hours after oxygen glucose deprivation, cells were stained for FACS analysis. The culture medium was removed and washed twice with HEPES buffer solution. 100 µl of 1× binding buffer (BB) solution (50 mM HEPES, 750 mM NaCl, 12.5 mM $CaCl_2$, 5 mM $MgCl_2$, 20% BSA) with 0.4 µl/ml Annexin V (Sigma-Aldrich, Poole, UK) was then added and left to incubate on ice for 10 minutes. Cells were then washed twice with 1×BB, and then 0.8 µg/ml propidium iodide (Sigma-Aldrich, Poole, UK) in 1% fetal bovine serum (FBS) in phosphate buffer solution (PBS) was added and left to incubate on ice for 5 minutes. This was followed with washing twice with 1% PBS in PBS and then adding 400 µl 0.25% trypsin/EDTA and left to incubate for 5 minutes at 37° C. 800 µl 1% FBS in PBS was then added to stop the reaction, cells were removed and added to tubes for centrifugation at 1200 g for 10 minutes. The supernatant was discarded and the cells were re-suspended with 300 µl 1% FBS in PBS. Steps, if possible, were performed on ice to reduce the amount of neuronal death.

Figure 9:
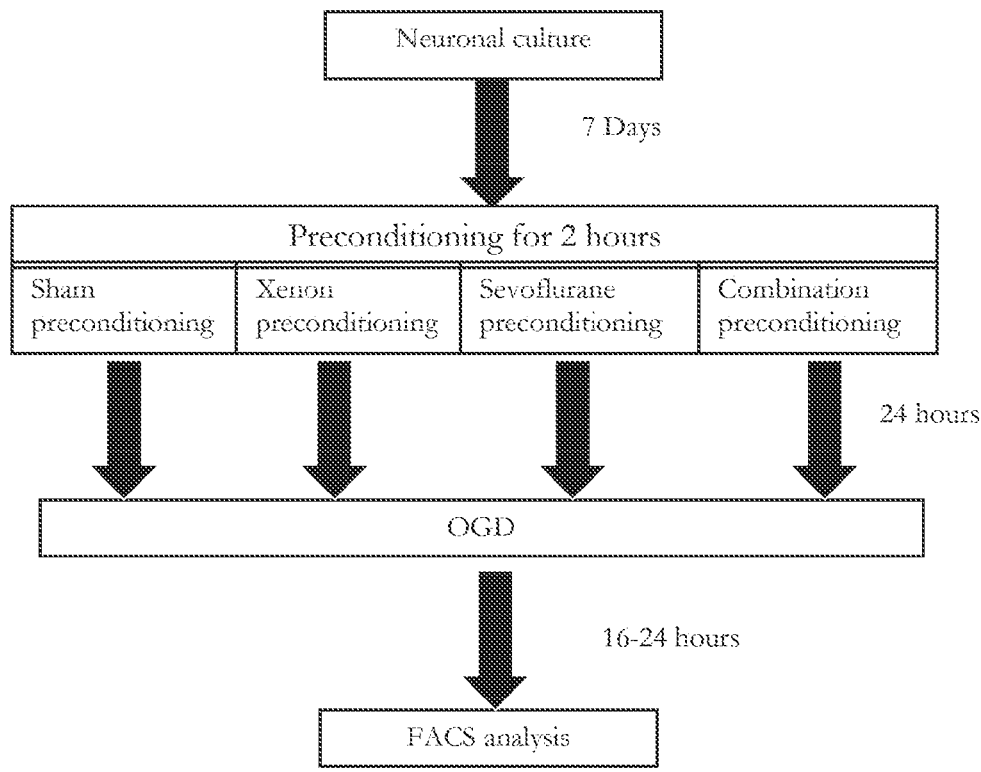
FIG. 9 shows the flow diagram of the protocol to assess the necrotic, viable and apoptotic cell populations after preconditioning.

A FACSCalibur (Becton Dickinson, Sunnyvale, Calif.) with a single argon laser was used for flow cytometric analysis. Excitation was carried out at 488 nm and the emission filters used were 515-545 BP (green; FITC) and 600LP (red; PI). At least 10,000 cells per sample were analysed. Data acquisition was performed with Cell Quest 3.3 (Becton Dickinson) and data analysis was performed with Cell Quest Pro (Becton Dickinson) (FIG. 9).

Statistical Analysis

Statistical analysis was performed using Instat. Data was expressed as mean+/−SEM. Statistical analysis of the data within and between groups was performed with analysis of variance for repeated measures followed by the Student-Newman-Keuls test. Results are considered to be significant if P<0.05.

Results

Xenon Preconditioning

Figure 10:
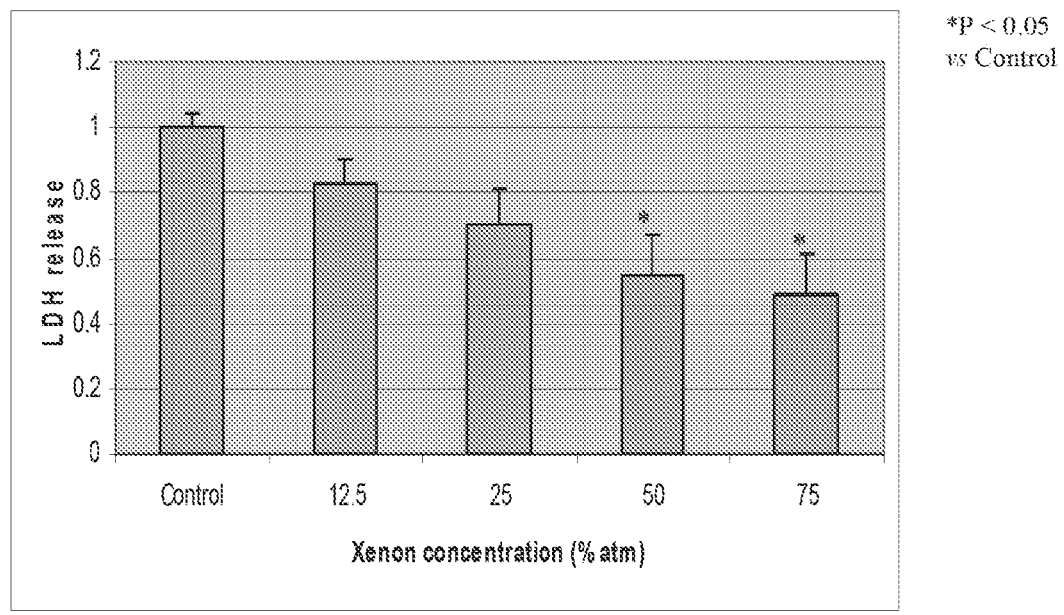
FIG. 10 shows the graph of LDH release against xenon concentration. The cells were preconditioned for 2 hours followed by OGD (oxygen glucose deprivation).

Preconditioning with xenon for 2 hours produces a concentration dependent reduction in LDH release following oxygen glucose deprivation (FIG. 10). LDH release was significantly reduced by xenon at 50% and at 75%, to 55+/−12% and to 49+/−12% of control values respectively (p<0.05). Xenon at 12.5% reduced LDH release to 83+/−7% and xenon at 25% reduced LDH release to 70+/−11% of controls. Xenon at 12.5% and 25% displayed a trend of decreasing LDH release with increasing concentrations, however the results were not significant (p>0.05).

Sevoflurane Preconditioning

Figure 11:
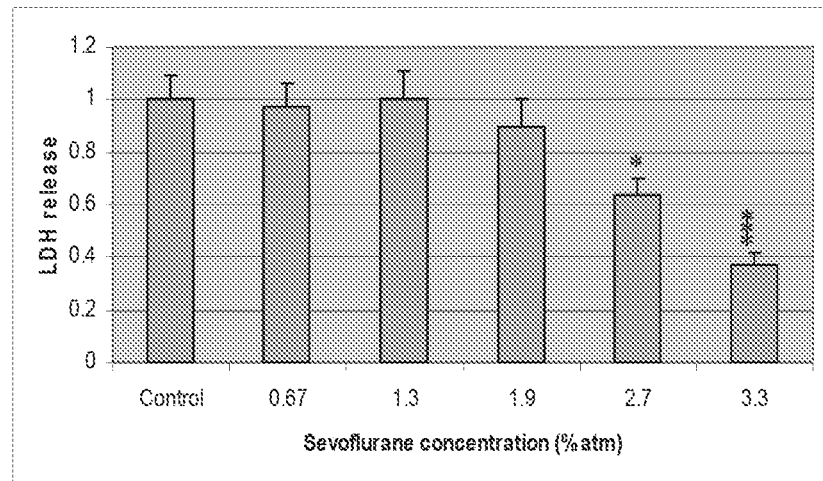
FIG. 11 shows the graph of LDH release against sevoflurane concentrations. The cells were preconditioned for 2 hours followed by OGD.

Sevoflurane preconditioning for 2 hours also produces a concentration dependent reduction in LDH release (FIG. 11). Concentrations of sevoflurane greater than 1.9% produced a significant reduction in LDH release. Concentrations of sevoflurane less than 1.9% did not significantly reduce LDH release and thus did not offer neuronal cells any protection from oxygen glucose deprivation (p>0.05). Sevoflurane at 2.7% resulted in a significant decrease of LDH to 64+/−6% of control (p<0.05). LDH release was maximally reduced at concentrations of 3.3% sevoflurane to 37+/−5% of controls (p<0.001). Sevoflurane at 0.67% was found to be ineffective, producing a reduction of LDH release to 97+/−5% of controls, and sevoflurane at 1.3% also did not produce any reduction in LDH release (100+/−11% of controls).

Xenon and Sevoflurane Combination Preconditioning

Figure 12:
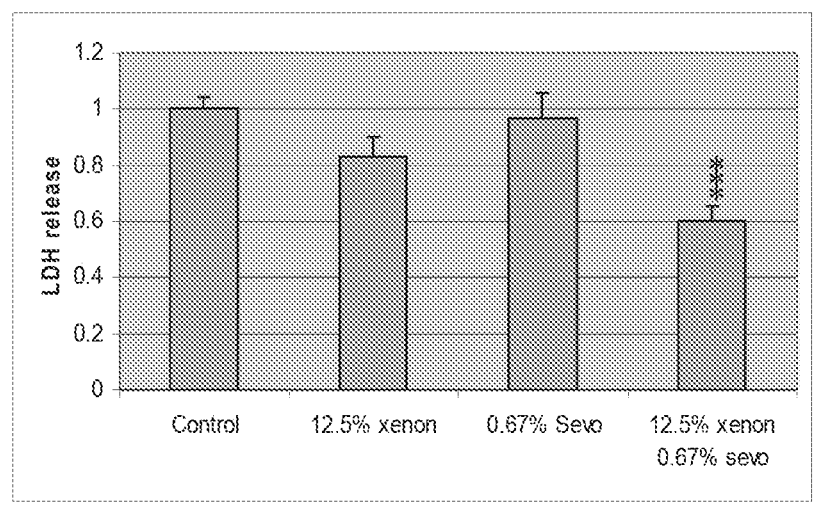
FIG. 12 shows the graph of LDH release against xenon preconditioning, sevoflurane preconditioning an combination of preconditioning. The cells were preconditioned for 2 hours followed by OGD.

Ineffective doses of xenon and sevoflurane in combination worked synergistically together resulting in a greater reduction in LDH release than corresponding concentrations of the gases used alone. In earlier experiments (FIG. 12), data showed that sevoflurane at 0.67% and xenon at 12.5% were found not to produce significant reduction in LDH release, and hence offered no significant protection from ischaemic damage (p>0.05). However when the two gases are used in combination as preconditioners, LDH release was significantly reduced to 59+/−5% of controls (p<0.001).

Assessment of Necrotic, Viable, and Apoptotic Cell Populations with Combination Preconditioning To extrapolate the mechanisms behind xenon, sevoflurane, and combination preconditioning, FACS was used to determine whether the gases exerts its effects via an anti-apoptotic or anti-necrotic mechanism. For this technique it is necessary to use pure neuronal cultures.

Figure 13:
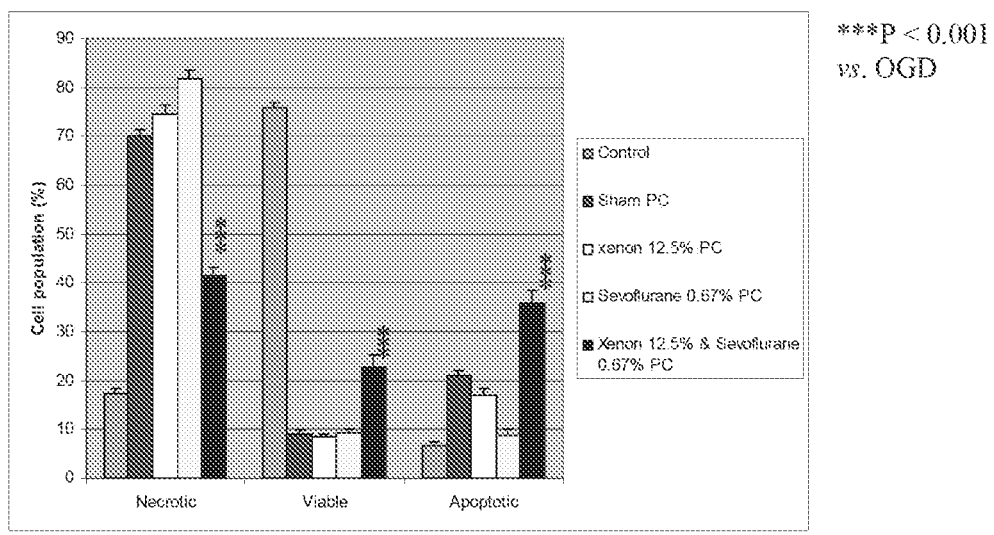
FIG. 13 shows combination preconditioning, using FACS analysis of necrotic, viable and apoptotic cell populations.

Controls were unstained cells with no injury and no preconditioning, in order to determine whether viable cells gave off fluorescence and to define a viable cell region. The effectiveness of xenon and sevoflurane combination used as preconditioners to reduce the amount of neuronal injury following oxygen glucose deprivation is consistent with data from the LDH assay (FIG. 13). Sham preconditioning (injured cells with no preconditioning), 12.5% xenon and 0.67% sevoflurane had a significantly smaller viable cell population compared to controls (p<0.001). Combination preconditioning had a viable cell population of 23+/−1%, confirming synergy of the two gases in reducing the amount of neuronal injury in an oxygen glucose deprivation model compared to 9% in 12.5% xenon and 0.67% sevoflurane (P<0.001).

Control groups had a necrotic population of 17+/−1%, whereas sham preconditioning, 12.5% xenon preconditioning, 0.67% sevoflurane preconditioning had necrotic populations of 70+/−2%, 75+/−2%, and 81+/−2% respectively. However xenon and sevoflurane in combination had a higher apoptotic population of 35%+/−3%, compared to xenon alone and sevoflurane alone, with apoptotic populations of 9+/−1% (p<0.001) and 17+/−1% (p<0.001) respectively.

A combination of xenon and sevoflurane had a significantly reduced necrotic cell population of 41+/−2% (p<0.001). These data suggest that xenon and sevoflurane when used in combination as preconditioners provide substantial neuroprotection through an anti-necrotic mechanism.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

REFERENCES

Aggleton J P, Brown M W (1999) Episodic memory, amnesia and the hippocampal-anterior thalamic axis. Behav Brain Sci 22(3):425-44

Amos R J, Amess J A, Hinds C J, Mollin D L (1982) Incidence and pathogenesis of acute megaloblastic bone-marrow change in patients receiving intensive care. Lancet 16; 2(8303):835-8

Anand K J, Scalzo F M (2000) Can adverse neonatal experiences alter brain development and subsequent behaviour? Biol. Neonate 77(2):69-82

Balduini W, De Angelis V, Mazzoni E, Cimino M (2000) Long-lasting behavioural alterations following a hypoxic/ischaemic brain injury in neonatal rats. Brain Research 859:318-325

Beas-Zárate C, Rivera-Huizar S V, Martinez-Contreras A, Feria-Velasco A, Armendariz-Borunda J (2001) Changes in NMDA-receptor gene expression are associated with neurotoxicity induced neonatally by glutamate in the rat brain. Neurochemistry International 39:1-10

Behar T N, Scott C A, Greene C L, Wen X, Smith S V, Maric D, Liu Q Y, Colton C A, Barker J L (1999) Glutamate Acting at NMDA Receptors Stimulates Embryonic Cortical Neuronal Migration. The Journal of Neuroscience 19(11):4449-44461

Behar T N, Smith S V, Kennedy R T, Mckenzie J M, Maric I, Barker J L (2001) $GABA_B$ Receptors Mediate Motility Signals for Migrating Embryonic Cortical Cells. Cerebral Cortex 11:744-753

Beltramino C A, de Olmos J S, Gallyas F, Heimer L, Zaborszky L (1993) Silver staining as a tool for neurotoxic assessment. NIDA Res Monogr. 136:101-26

Bhakar A L, Tannis L L, Zeindler C, Russo M P, Jobin C, Park D S, MacPherson S, Barker P A (2002) Constitutive Nuclear Factor-κB Activity Is Required for Central Neuron Survival. Journal of Neuroscience 22(19):8466-8475

Bittigau P, Sifringer M, Genz K, Reith E, Pospischil D, Govindarajalu S, Dzietko M, Pesditschek S, Mai I, Dikranian K, Olney J W, Ikonomidou C (2002) Antiepileptic drugs and apoptotic neurodegeneration in the developing brain. PNAS 99(23):15089-15094

Brenneman D E, Forsythe I D, Nicol T, Nelson P G (1990) N-methyl-D-aspartate receptors influence neuronal survival in developing spinal cord cultures. Brain Res Dev Brain Res 51(1):63-8

Brunet A, Datta S R, Greenberg M E (2001) Transcription-dependent and -independent control of neuronal survival by the PI3K-Akt signalling pathway. Current Opinion in Neurobiology 11:297-305

Butler A B (1999) Whence and whither cortex? TINS 22(8): 332-334

Clancy B, Darlington R B, Finlay B L (2001) Translating Developmental Time Across Mammalian Species. Neuroscience 105:7-17

Cullen S C, Gross E G (1951) The Anesthetic Properties of Xenon in Animals and Human Beings, with Additional Observations on Krypton. Science 113:580-582

Danysz W, Parsons C G (1998) Glycine and N-Methyl-D-Aspartate Receptors: Physiological Significance and Possible Therapeutic Applications. Pharmacological Reviews 50(4):597-664

Davis K M, Wu J Y (2001) Role of glutamatergic and GABAergic systems in alcoholism. J Biomed Sci 8(1):7-19

De Sousa S L M, Dickinson R, Lieb W R, Franks N P (2000) Contrasting Synaptic Actions of the Inhalational General Anesthetics Isoflurane and Xenon. Anesthesiology 92:1055-66

DeOlmos J S, Ingram W R (1971) An improved cupric-silver method for impregnation of axonal and terminal degeneration. Brain Res 33:523-529

Dikranian K, Ishimaru M J, Tenkova T, Labruyere J, Qin Y Q, Ikonomidous C, Olney J W (2001) Apoptosis in the in vivo Mammalian Forebrain. Neurobiology of Disease 8:359-379

Dingledine R and McBain C J (1999) Glutamate & Aspartate in: Siegel S J, Agranoff B W, Albers R W, Fisher S K, Uhler M D (Eds) Basic Neurochemistry: Molecular, Cellular & Medical Aspects, 6th Edition, Lippincott-Raven, pp 315-332

Dingley J, Ivanova-Stoilova T M, Grundler S, Wall T (1999) Xenon: recent developments. Anesthesia 54:335-346

Dobbing J, Sands J (1979) The brain growth spurt in various mammalian species. Early Hum Dev 3:79-84.

Dragunow M, Preston K (1995) The role of inducible transcription factors in apoptotic nerve cell death. Brain Research Reviews 21:1-28

Duckhyun K Y and Barr G A (1995) The induction of Fos-like immunoreactivity by noxious thermal, mechanical and chemical stimuli in the lumbar spinal cord of infant rats. Pain 60:257-265

Farber N B, Olney J W (2003) Drugs of abuse that cause developing neurons to commit suicide. Developmental Brain Research 147:37-45

Farber N B, Wozniak D F, Price M T, Labruyere J, Huss J, St. Peter H, Olney J W (1995) Age-Specific Neurotoxicity in the Rat Associated with NMDA Receptor Blockade: Potential Relevance to Schiozphrenia? Biol. Psychiatry 38:788-796

Forrest D, Yuzaki M, Soares H D, Ng L, Luk D C, Sheung M, Stewart C L, Morgan J I, Connor J A, Curran T (1994) Targeted disruption of NMDA receptor 1 gene abolishes NMDA response and results in neonatal death. Neuron 13(2):325-38

Frankiewicz T, Pilc A, Parsons C G (2000) Differential effects of NMDA-receptor antagonists on long-term potentiation and hypoxic/hypoglycemic excitotoxicity in hippocampal slices. Neuropharmacology 39:631-642

Franks N P, Dickinson R, de Sousa S L M, Hall A C, Lieb W R (1998) How does xenon produce anesthesia? Nature Vol 396:324

Frietsch T, Bogdanski R, Blobner M, Werner C, Kuschinsky W, Waschke K F (2001) Effects of Xenon on Cerebral Blood Flow and Cerebral Glucose Utilization in Rats. Anesthesiology 94:290-7

Fukura H, Kitani Y, Komiya Y, Igarashi M (2000) Nitrous Oxide, but not Xenon, Affects the Signalling in the Neuronal Growth Cone. Prog. Neuro-Psychopharmacol. & Biol. Psychiat. 24:1357-1368

Garcia I, Martinou I, Tsujimoto Y, Martinou J C (1992) Prevention of programmed cell death of sympathetic neurones by the bcl-2 protooncogene. Science 258(5080):302-4

Goen T, Kadish I, Wyss J M (2002) The role of the laterodorsal nucleus of the thalamus in spatial learning and memory in the rat. Behavioural Brain Research 136:329-337

Goto T, Yoshinori N, Morita S (2003) Will Xenon Be a Stranger of a Friend? Anesthesiology 98:1-2

Green D R (2000) Apoptotic pathways: paper wraps stone blunts scissors. Cell 102:1-4

Gyulai F E, Mintun M A, Firestone L L (2001) Dose-dependent Enhancement of In vivo $GABA_A$-Benzodiazepine Receptor Binding by Isoflurane. Anesthesiology 95:585-93

Haberny K, Paule M G, Scallet A C, Sistare F D, Lester D S, Hanig J P, Slikker W (2002) Ontogeny of the N-Methyl-D-Aspartate (NMDA) Receptor System and Susceptibility to Neurotoxicity. Toxicological Sciences 68:9-17

Hanne Marx T, Musati S, Santo M, Suwa K, Morita S (2001) Xenon: Uptake & Costs. International Anesthesiology Clinics 3:43-61

Hardingham G E, Bading H (2003) The Yin and Yang of NMDA receptor signalling. Trends in Neurosciences 26(2): 81-89

Hardingham G E, Fukunaga Y, Bading H (2002) Extrasynaptic NMDARs oppose synaptic NMDARs by triggering CREB shutoff and cell death pathways. Nature Neuroscience 5(5):405-414

Hasegawa K, Litt L, Espanol M T, Sharp F R, Chan P H (1998) Expression of c-fos and hsp70 mRNA in neonatal rat cerebrocortical clices during NMDA-induced necrosis and apoptosis. Brain Research 785:262-278

Homi, H. M., Yokoo, N., Ma, D., Warner, D. S., Franks, N. P., Maze, M. & Grocott, H. P. (2003). The neuroprotective effect of xenon administration during transient middle cerebral artery occlusion in mice. Anesthesiology 99, 876-81.

Hua J Y and Smith S J (2004) Neural activity and the dynamics of central nervous system development. Nature Neuroscience 7(4):327-332

Huber J D, Darling S F, Park K K, Soliman K F A (2001) The role of NMDA receptors in neonatal cocaine-induced neurotoxicity. Pharmacology, Biochemistry and Behaviour 69:451-459

Ikonomidou C, Bittigau P, Ishimaru M J, Wozniak D F, Koch C, Genz K, Price M T, Stefovska V, Hörster F, Tenkova T, Dikranian, Olney J W (2000) Ethanol-Induced Apoptotic Neurodegeneration and Fetal Alcohol Syndrome. Science 287:1056-1060

Ikonomidou C, Bittigau P, Koch C, Genz K, Hoerster F, Felderhoff-Mueser U, Tenkova T, Dikranian K, Olney J W (2001) Neurotransmitters and apoptosis in the developing brain. Biochemical Pharmacology 62:401-405

Ikonomidou C, Bosch F, Miksa M, Bittigau P, Vöckler J, Dikranian K, tenkova T I, Stefovska V, Turski L, Olney J W (1999) Blockade of NMDA Receptors and Apoptotic Neurodegeneration in the Developing Brain. Science 238:70-74

Ikonomidou C, Lechoslaw T (2002) Why did NMDA receptor antagonists fail clinical trials for stroke and traumatic brain injury? Lancet Neurology 1:383-386

Jevtovic-Todorovic V, Hartman R E, Yukitoshi I, Benshoff N D, Dikranian K, Zorumski C F, Olney J W, Wozniak D F (2003) Early Exposure to Common Anesthetic Agents Causes Widespread Neurodegeneration in the Developing Rat Brain and Persistent Learning Defects. The Journal of Neuroscience 23(3):876-882

Jevtovic-Todorovic V, Olney J W (2003) Neuroprotective Agents in: Evers A S, Maze M (Eds), Anesthetic Pharmacology: Physiological Principles & Clinical Practise, Churchill Livingstone pp 557-572

Jevtovic-Todorovic V, Todorovic S M, Mennerick S, Powell S, Dikranian K, Benshoff N, Zorumski C F, Olney J W (1998) Nitrous oxide (laughing gas) is an NMDA antagonist, neuroprotectant and neurotoxin. Nat Med 4(4):460-3

Kato K, Li S T, Zorumski C F (1999) Modulation of Long Term Potentiation Induction In The Hippocampus By N-Methyl-D-Aspartate-Mediated Presynaptic Inhibition. Neuroscience 92(4): 1261-1272

Kerr J F, Wyllie A H, Currie A R (1972) Apoptosis: a basic biological phenomenon with wide-ranging implications in tissue kinetics. Br J Cancer 26(4):239-57

Komuro H, Rakie P (1993) Modulation of neuronal migration by NMDA receptors. Science 260(5104):95-7

Korsmeyer S J, Wei M C, Saito M, Weller S, Oh K J, Schlesinger P H (2002) Pro-apoptotic cascade activates BID, which oligomerizes BAK or BAC into pores that result in the release of cytochrome c. Cell Death and Differentiation 7:1166-1173

Kubo T, Yokoi T, Hagiwara Y, Fukumori R, Goshima Y, Misu Y (2001) Characteristics of protective effects on NMDA antagonist and calcium channel antagonist on ischemic calcium accumulation in rat hippocampal CA1 region. Brain Research Bulletin 54(4):413-419

Lane G A, Nahrwold M L, Tait A R, Taylor-Busch M, Cohen P J, Beaudoin A R (1980) Anesthetics as teratogens: $N_2O$ is fetotoxic, xenon is not. Science 210(4472):899-901

Layzer R B (1978) Myeloneuropathy after prolonged exposure to nitrous oxide. Lancet 9; 2(8108):1227-30

Li Y, Erzurumlu R S, Chen C, Jhaveri S, Tonegawa S (1994) Whisker-related neuronal patterns fail to develop in the trigeminal brainstem nuclei of NMDAR1 knockout mice. Cell 76(3):427-37

Lipsky R H, Xu K, Zhu D, Kelly C, Terhakopian A, Novelli A, Marini A M (2001) Nuclear factor κB is a critical determinant in N-methyl-D-aspartate receptor mediated neuroprotection. Journal of Neurochemistry 78:254-264.

Lipton S A, Nakanishi N (1999) Shakespear in love-with NMDA receptors? Nature Medicine 5(3):270-271

Luttropp H H, Thomasson R, Dahm S, Persson J, Werner O (1994) Clinical experience with minimal flow xenon anesthesia. Acta Anesthesiol. Scand. 38(2):121-5

Lynch C, Baum J, Tenbrinck R (2000) Xenon Anesthesia. Anesthesiology 92:865-70

Ma D, Hossain M, Rajakumaraswamy N, Franks N P, Maze M (2003a) Combination of Xenon and Isoflurane Produces a Synergistic Protective Effect against Oxygen-Glucose Deprivation Injury in a Neuronal-Glial Co-culture Model. Anesthesiology 99:748-51

Ma D, Sanders R D, Halder S, Rajakumaraswamy N, Franks N P, Maze M (2004) Xenon Exerts Age-independent Antinociception in Fischer Rats. Anesthesiology 100:1313-18

Ma D, Wilhelm S, Maze M, Franks N P (2002) Neuroprotective and neurotoxic properties of the 'inert' gas xenon. British Journal of Anesthesia 89(5):739-46

Ma D, Yang H, Lynch J, Franks N P, Maze M, Grocott H P (2003b) Xenon Attenuates Cardiopulmonary Bypass-induced Neurologic and Neurocognitive Dysfunction in the Rat. Anesthesiology 98:690-8

Ma, D., Hossain, M., Chow, A., Arshad, M., Battson, R. M., Sanders, R. D., Mehmet, H., Edwards, A. D., Franks, N. P. & Maze, M. (2005). Xenon and hypothermia combine to provide neuroprotection from neonatal asphyxia. Ann Neurol, 58, 182-93.

Malhotra A K, Pinals D A, Weingartner H, Sirocco K, Missar C D, Pickar D, Breier A (1996) NMDA Receptor Function and Human Cognition: The Effects of Ketamine in Healthy Volunteers. Neuropsychopharmacology 14(5):301-307

Martin L J, Al-Abdulla N A, Brambrink A M, Kirsch J R, Sieber F E, Portera-Cailliau (1998) Neurodegeneration in excitoxicity, global cerebral ischaemia, and target deprivation: A perspective on the contributions of apoptosis and necrosis. Brain Research Bulletin 46(4):281-309

Martinou J C, Dubois-Dauphin M, Staple J K, Rodriguez I, Frankowski H, Missotten M, Albertini P, Talabot D, Catsicas S, Pietra C (1994) Overexpression of bcl-2 in transgenic mice protects neurones from naturally occurring cell death and experimental ischaemia. Neuron 13(4): 1017-30

Mayumi Homi H, Yokoo N, Ma D, Warner D S, Franks N P, Maze M, Grocott H P (2003) The Neuroprotective Effect of Xenon Administration during Transient Middle Cerebral Artery Occlusion in Mice. Anesthesiology 99:876-81

Molnar Z, Blakemore C (1995) How do thalamic axons find their way to the cortex? Trends Neurosci. 18(9):389-97

Monti B, Contestabile A (2000) Blockade of the NMDA receptor increases developmental apoptotic elimination of granule neurons and activates caspases in the rat cerebellum. European Journal of Neuroscience 12:3117-3123

Moore K L and Persaud T V N (Eds), Human Birth Defects in: The Developing Human: Clinically Orientated Embryology ($6^{th}$ Edition), 1998, WB Saunders Company, pp 167-200

Motoyama N, Wang F, Roth K A, Sawa H, Nakayama K, Nakayama K, Negishi I, Senju S, Zhang Q, Fujii S (1995) Massive cell death of immature hematopoietic cells and neurons in Bcl-x deficient mice. Science 267:1506-1510

Nagata A, Nakao S, Nishizawa N, Masuzawa M, Inada T, Murao K, Miyamoto E, Shingu K (2001) Xenon Inhibits but $N_2O$ Enhances Ketamine-Induced c-Fos Expression in the Rat Posterior Cingulate and Retrosplenial Cortices. Anesth Analg 92:362-8

Nakata Y, Goto T, Morita S (1997) Comparison of inhalation inductions with xenon and sevofurane. Acta Anesthesiol Scand 41:1157-61

Nakata Y, Goto T, Saito H, Ishiguro Y, Terui K, Kawakami H, Tsuruta Y, Niimi Y, Morita S (2000) Plasma concentration of fentanyl with xenon to block somatic and hemodynamic responses to surgical incision. Anesthesiology 92:1043-8

Newcomer J W, Krystal J H (2001) NMDA receptor regulation of memory and behavior in humans. Hippocampus 11(5):529-42

O'Callaghan J P, Jensen K F (1992) Enhanced expression of glial fibrillary acidic protein and the cupric silver degeneration reaction can be used as sensitive and early indicators of neurotoxicity. Neurotoxicology 13(1):113-22

Okabe S, Kim H D, Miwa A, Kuriu T, Okado H (1999) Continual remodeling of post-synaptic densities and it's regulation by synaptic activity. Nat. Neuroscience 2:804-811

Oliet S H R, Piet R, Poulain D A (2001) Control of Glutamate Clearance and Synaptic Efficacy by Glial Coverage of Neurones. Science 292:923-926

Olney J W (1969) Brain lesions, obesity & other disturbances in mice treated with monosodium glutamate. Science 164 (880):719-21

Olney J W (2002a) New insights and issues in developmental neurotoxicology. Neurotoxicology 23(6): 659-68

Olney J W, Tenkova T, Dikranian K, Muglia L J, Jermakowicz W J, D'Sa C, Roth K A (2002b) Ethanol-Induced Caspase-3 Activation in the in vivo Developing Mouse Brain. Neurobiology of Disease 9:205-219

Olney J W, Wozniak D F, Farber N B, Jevtovic-Todorovic V, Bittigau P, Ikonomidou C (2002c) The enigma of fetal alcohol neurotoxicity. Ann Med 34(2):109-19

Olney J W, Wozniak D F, Jevtovic-Todorovic V, Farber N B, Bittigau P, Ikonomidou C (2002d) Drug-induced apoptotic neurodegeneration in the developing brain. Brain Pathol 12(4):488-98

Olsen R W and DeLorey T M (1999) GABA & Glycine in: Siegel S J, Agranoff B W, Albers R W, Fisher S K, Uhler M D (Eds) Basic Neurochemistry: Molecular, Cellular & Medical Aspects, 6th Edition, Lippincott-Raven, pp 336-346

Philpot B D, Sekhar A K, Shouvai H Z, Bear M F (2001) Visual Experience and Deprivation Bidirectionally Modify the Composition and Function of NMDA Receptors in the Visual Cortex. Neuron 29:157-169

Pohl D, Bittigau P, Ishimaru M J, Stadthaus D, Hübner C, Olney J W, Turski L, Ikonomidou C (1999) N-Methyl-D- aspartate antagonists and apoptotic cell death triggered by head trauma in developing rat brain. Proc. Natl. Acad. Sci. USA 96:2508-2513

Rinkenberger J L, Horning S, Klocke B, Roth K, Korsmeyer S J (2000) Mcl-1 deficiency results in peri-implantation embryonic lethality. Genes & Development 14:23-27

Sanders R D, Franks N P, Maze M (2003) Xenon: no stranger to anesthesia. British Journal of Anesthesia 91(5):709-17

Scheetz A J, Nairn A C, Constantine-Paton M (2000) NMDA receptor-mediated control of protein synthesis at developing synapses. Nature Neuroscience 3(3)

Schmidt M, Marx T, Kotzerke J, Lüderwald S, Armbruster S, Topalidis P, Schirmer U, Reinelt H (2001) Cerebral and regional organ perfusion in pigs during xenon anesthesia. Anesthesia 56:1154-1159

Schmidt, M., Marx, T., Gloggl, E., Reinelt, H. & Schirmer, U. (2005). Xenon attenuates cerebral damage after ischemia in pigs. Anesthesiology, 102, 929-36.

Sherrard R M, Bower A J (1998) Role of afferents in the development and cell survival of the vertebrate nervous system. Clin Exp Pharmacol Physiol 25(7-8):487-95

Shichino T, Murakawa M, Adachi T, Miyazaki Y, Segawa H, Fukuda K, Mori K (2002) Effects of xenon on acetylcholine release in the rat cerebral cortex in vivo. British Journal of Anesthesia 88)6):866-8

Sloviter R S (2002) Apoptosis: a guide for the perplexed. TRENDS in Pharmacological Sciences 23(1):19-24

Stowe D F, Rehmert G C, Kwok W M, Weigt H U, Georgieff M, Bosnjak Z J (2000) Xenon Does Not Alter Cardiac Function or Major Cation Current in Isolated Guinea Pig Hearts or Myocytes. Anesthesiology 92:516-22

Tokuyama S, Zhu H, Oh S, Ho I K, Yamamoto T (2001) Further evidence for a role of NMDA receptors in the locus coeruleus in the expression of withdrawal syndrome from opioids. Neurochemistry International 39:103-109

Tsai G, Coyle J T (1998) The Role of Glutamatergic Neurotransmission in the Pathophysiology of Alcoholism. Annu Rev Med 49:173-84

Wagey R, Hu J, Pelech S L, Raymond L A, Krieger C (2001) Modulation of NMDA-mediated excitotoxicity by protein kinase C. Journal of Neurochemistry 78:715-726

Walton M, MacGibbon G, Young D, Sirimanne E, Williams C, Gluckman P, Dragunow M (1998) Do c-Jun, c-Fos and Amyloid Precursor Protein Play a Role in Neuronal Death or Survival? Journal of Neuroscience Research 53:330-342

Wilhelm S, Ma D, Maze M, Franks N P (2002) Effects of Xenon on In Vitro and In vivo Models of Neuronal Injury. Anesthesiology 96:1485-91

Williams D G, Howard R F (2003) Epidural analgesia in children. A survey of current opinions and practises amongst UK paediatric anesthetists. Paediatric Anesthesia 13:769-776

Wisden W, Errington M L, Williams S, Dunnett S B, Waters C, Hitchcock D, Evan G, Bliss T V, Hunt S P (1990) Differential expression of intermediate early genes in the hippocampus & spinal cord. Neuron 4(4):603-14

Yoshida H, Kong Y, Yoshida R, Elia A J, Hakem A, Hakem R, Penninger J M, Mak T W (1998) Apaf-1 Is Required for Mitochondrial Pathway of Apoptosis and Brain Development. Cell 94:739-750

Young C, Klocke B J, Tenkova T, Choi J, Labruyere J, Qin Y Q, Holtzman D M, Roth K A, Olney J W (2003) Ethanol-induced neuronal apoptosis in vivo requires BAX in the developing mouse brain. Cell Death and Differentiation 10:1148-1155

Young D, Lawlor P A, Leone P, Dragunow M, During M J (1999) Environmental enrichment inhibits spontaneous apoptosis, prevents seizures and is neuroprotective. Nature Med 5:448-53

Young, T. Tenkova, H. H. Wang, Y. Q. Qin, J. Labuyere, V. Jevtovic-Todorovic, J. W. Olney (2003) A single sedating dose of ketamine, causes neuronal apoptosis in developing mouse brain, Society for Neuroscience Abstract (in press).

Yuan J, Yankner B A (2000) Apoptosis in the nervous system. Nature 407:802-809.

The invention claimed is:

1. A method of reducing the severity of a neurological deficit, the method comprising administering a therapeutically effective amount of xenon and a GABAergic agent to a subject at risk of suffering the neurological deficit, wherein the xenon and the GABAergic agent are administered to the subject in a gas comprising from 10-20% xenon and 0.67%-4% GABAergic agent, wherein the reducing the severity comprises maintaining more viable neurons, relative to neurons in a control, after exposure to a stimulus that causes the neurological deficit.

2. The method of claim 1, wherein the neurological deficit is associated with neuronal apoptosis, neuronal necrosis, or neuronal injury.

3. The method of claim 1, wherein the GABAergic agent is isoflurane, sevoflurane or desflurane.

4. The method of claim 1, wherein the GABAergic agent is isoflurane, and the neurological deficit is associated with hypoxia.

5. The method of claim 1, wherein the GABAergic agent is sevoflurane, and the neurological deficit is associated with hypoxia.

6. The method of claim 1, wherein the GABAergic agent is desflurane, and the neurological deficit is associated with hypoxia.

7. The method of claim 1, wherein the control comprises a value obtained by measuring viability of neurons exposed to the stimulus of the neurological deficit but not exposed to the gas.

8. The method of claim 7, wherein the stimulus of the neurological deficit comprises exposing the neurons to a hypoxic condition.

* * * * *